(12) United States Patent
Niedermeyer

(10) Patent No.: US 12,610,952 B2
(45) Date of Patent: Apr. 28, 2026

(54) ANTIMICROBIAL COMPOSITIONS AND METHODS

(71) Applicant: EVOQ NANO, INC., Salt Lake City, UT (US)

(72) Inventor: William Harold Niedermeyer, West Jordan, UT (US)

(73) Assignee: EVOQ NANO, INC., Salt Lake City, UT (US)

( * ) Notice: Subject to any disclaimer, the term of this patent is extended or adjusted under 35 U.S.C. 154(b) by 668 days.

(21) Appl. No.: 17/878,652

(22) Filed: Aug. 1, 2022

(65) Prior Publication Data

US 2022/0386619 A1 Dec. 8, 2022

Related U.S. Application Data

(60) Continuation-in-part of application No. 16/012,508, filed on Jun. 19, 2018, now abandoned, which is a division of application No. 14/861,243, filed on Sep. 22, 2015, now abandoned.

(60) Provisional application No. 62/054,154, filed on Sep. 23, 2014, provisional application No. 62/054,152, filed on Sep. 23, 2014.

(51) Int. Cl.
| | |
|---|---|
| *A01N 59/16* | (2006.01) |
| *A61K 33/24* | (2019.01) |
| *A61K 33/242* | (2019.01) |
| *A61K 33/243* | (2019.01) |
| *A61K 33/244* | (2019.01) |

(52) U.S. Cl.
CPC .............. *A01N 59/16* (2013.01); *A61K 33/24* (2013.01); *A61K 33/242* (2019.01); *A61K 33/243* (2019.01); *A61K 33/244* (2019.01)

(58) Field of Classification Search
CPC .......... A01N 59/16; A61K 33/242; A01P 1/00
See application file for complete search history.

(56) References Cited

U.S. PATENT DOCUMENTS

| | | | |
|---|---|---|---|
| 3,133,023 | A | 5/1964 | Vogel |
| 4,121,017 | A | 10/1978 | Dougherty et al. |
| 4,515,740 | A | 5/1985 | Schuettenberg et al. |
| 5,047,448 | A | 9/1991 | Tanaka et al. |
| 5,227,608 | A | 7/1993 | Yoshida et al. |
| 5,390,864 | A | 2/1995 | Alexander |
| 5,585,020 | A | 12/1996 | Becker et al. |
| 5,677,075 | A | 10/1997 | Fujita |
| 6,051,279 | A | 4/2000 | Gualco et al. |
| 6,232,264 | B1 | 5/2001 | Lukehart et al. |
| 6,239,453 | B1 | 5/2001 | Yamada et al. |
| 6,509,070 | B1 | 1/2003 | Voevodin et al. |
| 6,660,379 | B1 | 12/2003 | Lakowicz et al. |
| 6,720,006 | B2 | 4/2004 | Hanke et al. |
| 7,014,737 | B2 | 3/2006 | Harutyunyan et al. |

| | | | |
|---|---|---|---|
| 7,252,814 | B2 | 8/2007 | De et al. |
| 7,332,351 | B2 | 2/2008 | Tan et al. |
| 7,371,457 | B2 | 5/2008 | Oldenburg et al. |
| 7,374,730 | B2 | 5/2008 | Simard et al. |
| 7,384,560 | B2 | 6/2008 | Martens et al. |
| 7,449,679 | B2 | 11/2008 | Plewa et al. |
| 7,509,993 | B1 | 3/2009 | Turng et al. |
| 7,527,824 | B2 | 5/2009 | Becker et al. |
| 7,553,801 | B2 | 6/2009 | Alexander et al. |
| 7,625,637 | B2 | 12/2009 | Kim |
| 7,662,731 | B2 | 2/2010 | Itoh et al. |
| 7,682,970 | B2 | 3/2010 | Grigoropoulos et al. |
| 7,700,032 | B1 | 4/2010 | Lu et al. |
| 7,884,160 | B2 | 2/2011 | Wang et al. |
| 7,967,876 | B2 | 6/2011 | Aradi et al. |
| 7,985,367 | B2 | 7/2011 | Hiromatsu et al. |
| 8,097,233 | B2 | 1/2012 | Porterat |
| 8,435,602 | B1 | 5/2013 | Seal |
| 8,490,583 | B1 | 7/2013 | Gardenier |
| 8,490,586 | B2 | 7/2013 | Ross et al. |
| 8,524,139 | B2 | 9/2013 | Toth et al. |
| 8,545,577 | B2 | 10/2013 | Tock et al. |
| 8,685,293 | B1 | 4/2014 | Coppa et al. |
| 8,709,531 | B2 | 4/2014 | Miller |
| 8,802,234 | B2 | 8/2014 | Che et al. |
| 8,883,865 | B2 | 11/2014 | Difrancesco et al. |
| 8,992,815 | B2 | 3/2015 | Hu et al. |
| 9,259,407 | B2 | 2/2016 | Baker et al. |
| 9,434,006 | B2 | 9/2016 | Niedermeyer |
| 9,463,510 | B2 | 10/2016 | Hendi et al. |
| 9,512,377 | B2 | 12/2016 | Binder et al. |
| 9,627,713 | B2 | 4/2017 | Moganty et al. |
| 9,839,652 | B2 | 12/2017 | Tarbet et al. |
| 9,849,512 | B2 | 12/2017 | Niedermeyer |
| 9,883,670 | B2 | 2/2018 | Niedermeyer |

(Continued)

FOREIGN PATENT DOCUMENTS

| | | |
|---|---|---|
| CA | 2560837 A1 | 3/2007 |
| CN | 101128550 A | 2/2008 |

(Continued)

OTHER PUBLICATIONS

Sahu et al., "Flower Shaped Silver Nanostructures: An Efficient Bacteria Exterminator", A Search for Antibacterial Agents; Chapter 2; [online] retrieved from: http://www.intechopen.com/books/a-search-forantibacterial-agents; 2007; 73(6): 1712-1720 (Year: 2007).*

(Continued)

*Primary Examiner* — Andrew S Rosenthal
(74) *Attorney, Agent, or Firm* — Workman Nydegger

(57) ABSTRACT

Antimicrobial compositions for killing or deactivating microbes, such as viruses, bacteria, or fungi, include metal nanoparticles, a carrier, and a plurality of metal nanoparticles. The nanoparticles can be selected to have a particle size and particle size distribution to selectively and preferentially kill one of a virus, a bacterium, or a fungus. Antiviral compositions can include nanoparticles having a particle size of 8 nm or less, 1-7 nm, 2-6.5 nm, or 3-6 nm. Antibacterial compositions can include nanoparticles having a particle size of 3-14 nm, 5-13 nm, 7-12 nm, or 8-10 nm. Antifungal compositions can include nanoparticles having a particle size of 9-20 nm, 10-18 nm, 11-16 nm, or 12-15 nm.

17 Claims, 11 Drawing Sheets

(56) References Cited

U.S. PATENT DOCUMENTS

| | | | |
|---|---|---|---|
| 9,885,001 B2 | 2/2018 | Niedermeyer |
| 9,919,363 B2 | 3/2018 | Niedermeyer |
| 10,099,191 B1 | 10/2018 | Lu et al. |
| 10,774,429 B2 | 9/2020 | Tarbet et al. |
| 11,018,376 B2 | 5/2021 | Niedermeyer |
| 11,646,453 B2 | 5/2023 | Niedermeyer |
| 2001/0031564 A1 | 10/2001 | Suzuki et al. |
| 2002/0051823 A1 | 5/2002 | Yan et al. |
| 2003/0012686 A1 | 1/2003 | Andresen et al. |
| 2003/0086859 A1 | 5/2003 | Kawakami et al. |
| 2003/0102099 A1 | 6/2003 | Yadav et al. |
| 2003/0108612 A1 | 6/2003 | Xu et al. |
| 2003/0129320 A1 | 7/2003 | Yu |
| 2003/0182972 A1 | 10/2003 | Reher et al. |
| 2003/0228525 A1 | 12/2003 | Kozawa et al. |
| 2004/0103936 A1 | 6/2004 | Andriessen |
| 2004/0214001 A1 | 10/2004 | Oldenburg et al. |
| 2005/0061779 A1 | 3/2005 | Blumenfeld et al. |
| 2005/0061785 A1 | 3/2005 | Schroder et al. |
| 2005/0153071 A1 | 7/2005 | Bouvrette et al. |
| 2005/0158506 A1 | 7/2005 | Waki et al. |
| 2005/0247866 A1 | 11/2005 | Plewa et al. |
| 2005/0258149 A1 | 11/2005 | Glukhoy et al. |
| 2005/0260276 A1 | 11/2005 | Yang et al. |
| 2006/0049034 A1 | 3/2006 | Lee et al. |
| 2006/0142853 A1 | 6/2006 | Wang et al. |
| 2007/0003603 A1 | 1/2007 | Karandikar et al. |
| 2007/0029185 A1 | 2/2007 | Tung |
| 2007/0125196 A1 | 6/2007 | Zhong et al. |
| 2007/0140951 A1 | 6/2007 | O'Brien et al. |
| 2007/0141259 A1 | 6/2007 | House et al. |
| 2007/0207335 A1 | 9/2007 | Karandikar et al. |
| 2007/0269576 A1 | 11/2007 | Barton et al. |
| 2007/0287202 A1 | 12/2007 | Maehashi et al. |
| 2008/0006524 A1 | 1/2008 | Liu et al. |
| 2008/0035682 A1 | 2/2008 | Coffey et al. |
| 2008/0044148 A1 | 2/2008 | Robinson et al. |
| 2008/0050448 A1 | 2/2008 | Wilson et al. |
| 2008/0143021 A1 | 6/2008 | Ehrentraut et al. |
| 2008/0161631 A1 | 7/2008 | Axtell et al. |
| 2008/0241490 A1 | 10/2008 | Newman et al. |
| 2008/0263940 A1 | 10/2008 | Parish et al. |
| 2008/0292673 A1 | 11/2008 | Crudden |
| 2009/0000186 A1 | 1/2009 | Sanders et al. |
| 2009/0028947 A1 | 1/2009 | Rahman Nia |
| 2009/0039316 A1 | 2/2009 | Hirai et al. |
| 2009/0061230 A1 | 3/2009 | Berkei et al. |
| 2009/0104179 A1 | 4/2009 | Boyden et al. |
| 2009/0117268 A1 | 5/2009 | Lewis et al. |
| 2009/0148484 A1 | 6/2009 | Lin et al. |
| 2009/0175948 A1* | 7/2009 | Jiang .................... A61K 9/5115 |
| | | 424/490 |
| 2009/0191288 A1 | 7/2009 | Squires |
| 2009/0214766 A1 | 8/2009 | Magdassi et al. |
| 2009/0246530 A1 | 10/2009 | Murakami et al. |
| 2010/0040655 A1 | 2/2010 | Ren et al. |
| 2010/0050872 A1 | 3/2010 | Lee |
| 2010/0068299 A1 | 3/2010 | Van et al. |
| 2010/0072645 A1 | 3/2010 | Hiromatsu et al. |
| 2010/0080957 A1 | 4/2010 | Chinn et al. |
| 2010/0092367 A1 | 4/2010 | Porterat |
| 2010/0154591 A1 | 6/2010 | Islam |
| 2010/0167958 A1 | 7/2010 | Lin et al. |
| 2010/0172997 A1 | 7/2010 | Omary et al. |
| 2010/0180413 A1 | 7/2010 | Jeong |
| 2010/0183739 A1 | 7/2010 | Newman |
| 2010/0187091 A1 | 7/2010 | Pierce et al. |
| 2010/0196192 A1 | 8/2010 | Liu et al. |
| 2010/0212221 A1 | 8/2010 | Aradi |
| 2010/0255110 A1 | 10/2010 | Yoon et al. |
| 2010/0272650 A1 | 10/2010 | Tsukada et al. |
| 2010/0272770 A1 | 10/2010 | De et al. |
| 2010/0301013 A1 | 12/2010 | Conneely et al. |
| 2011/0039078 A1 | 2/2011 | Brennan et al. |
| 2011/0052460 A1 | 3/2011 | Coffey et al. |

| | | | |
|---|---|---|---|
| 2011/0129536 A1 | 6/2011 | Donati et al. |
| 2011/0155643 A1 | 6/2011 | Tov et al. |
| 2011/0192450 A1 | 8/2011 | Liu et al. |
| 2011/0193025 A1 | 8/2011 | Ichikawa et al. |
| 2011/0196044 A1 | 8/2011 | Hu et al. |
| 2011/0197369 A1 | 8/2011 | Hinestroza et al. |
| 2011/0201527 A1 | 8/2011 | Lin et al. |
| 2011/0206753 A1 | 8/2011 | Karpov et al. |
| 2011/0228890 A1 | 9/2011 | Dean et al. |
| 2011/0244056 A1 | 10/2011 | Santra |
| 2011/0297653 A1 | 12/2011 | Ehrentraut et al. |
| 2012/0070729 A1 | 3/2012 | Wertz et al. |
| 2012/0088066 A1 | 4/2012 | Aytug et al. |
| 2012/0094036 A1 | 4/2012 | Droege et al. |
| 2012/0124899 A1 | 5/2012 | Difrancesco et al. |
| 2012/0136164 A1 | 5/2012 | Ying et al. |
| 2012/0138347 A1 | 6/2012 | Bahnmueller et al. |
| 2012/0138862 A1 | 6/2012 | Hogan |
| 2012/0164073 A1 | 6/2012 | Xu et al. |
| 2012/0174472 A1 | 7/2012 | Mills |
| 2012/0183674 A1 | 7/2012 | Bonn-Savage et al. |
| 2012/0225021 A1 | 9/2012 | Qian et al. |
| 2012/0301528 A1 | 11/2012 | Uhlmann et al. |
| 2012/0301531 A1 | 11/2012 | Uhlmann et al. |
| 2012/0313200 A1 | 12/2012 | Jackrel et al. |
| 2012/0328701 A1 | 12/2012 | Edelson et al. |
| 2013/0001833 A1* | 1/2013 | Niedermeyer ......... B82Y 40/00 |
| | | 264/400 |
| 2013/0078510 A1 | 3/2013 | Reynolds et al. |
| 2013/0116369 A1 | 5/2013 | Qi et al. |
| 2013/0152823 A1 | 6/2013 | Fouda et al. |
| 2013/0203849 A1 | 8/2013 | Ben Yehuda |
| 2013/0224477 A1 | 8/2013 | Xu et al. |
| 2013/0273116 A1 | 10/2013 | Jespersen et al. |
| 2013/0334104 A1 | 12/2013 | Halas et al. |
| 2013/0337189 A1 | 12/2013 | Miller |
| 2013/0337998 A1 | 12/2013 | Irving et al. |
| 2014/0024026 A1 | 1/2014 | Alocilja et al. |
| 2014/0178513 A1 | 6/2014 | Matthews |
| 2014/0221543 A1 | 8/2014 | Wang et al. |
| 2014/0274830 A1 | 9/2014 | Pol et al. |
| 2014/0288194 A1 | 9/2014 | Niedermeyer |
| 2014/0322351 A1 | 10/2014 | Gawande et al. |
| 2014/0370293 A1 | 12/2014 | Johnson |
| 2015/0008313 A1 | 1/2015 | Loboda et al. |
| 2015/0030919 A1 | 1/2015 | Kozawa et al. |
| 2015/0066135 A1 | 3/2015 | Weber et al. |
| 2015/0190550 A1 | 7/2015 | Nusko et al. |
| 2016/0081346 A1 | 3/2016 | Niedermeyer |
| 2016/0081347 A1 | 3/2016 | Niedermeyer |
| 2016/0082513 A1 | 3/2016 | Niedermeyer |
| 2016/0082514 A1 | 3/2016 | Niedermeyer |
| 2016/0083146 A1 | 3/2016 | Han |
| 2016/0083665 A1 | 3/2016 | Niedermeyer |
| 2016/0083901 A1 | 3/2016 | Niedermeyer |
| 2016/0144350 A1 | 5/2016 | Aizenberg et al. |
| 2016/0287631 A1 | 10/2016 | Tarbet et al. |
| 2016/0298243 A1 | 10/2016 | Tarbet et al. |
| 2016/0372243 A1 | 12/2016 | Cassignol et al. |
| 2017/0129975 A1 | 5/2017 | Hallinan et al. |
| 2017/0136112 A1 | 5/2017 | Pillich et al. |
| 2017/0166485 A1 | 6/2017 | Hong et al. |
| 2017/0209490 A1 | 7/2017 | Niedermeyer |
| 2018/0078580 A1 | 3/2018 | Tarbet et al. |
| 2018/0126463 A1 | 5/2018 | Niedermeyer |
| 2018/0282852 A1 | 10/2018 | Soloway |
| 2018/0368417 A1 | 12/2018 | Niedermeyer |
| 2019/0165426 A1 | 5/2019 | Niedermeyer |
| 2019/0225498 A1 | 7/2019 | Ruiz et al. |

FOREIGN PATENT DOCUMENTS

| | | | |
|---|---|---|---|
| CN | 101180372 A | 5/2008 |
| CN | 101415644 A | 4/2009 |
| CN | 101716684 A | 6/2010 |
| CN | 101932752 A | 12/2010 |
| CN | 101960070 A | 1/2011 |
| CN | 102120619 A | 7/2011 |
| CN | 102753628 A | 10/2012 |

(56) References Cited

FOREIGN PATENT DOCUMENTS

| CN | 103700898 A | 4/2014 |
|---|---|---|
| CN | 103796946 A | 5/2014 |
| CN | 103891558 A | 7/2014 |
| CN | 103917546 A | 7/2014 |
| CN | 104014811 A | 9/2014 |
| CN | 107107199 A | 8/2017 |
| CN | 108091834 A | 5/2018 |
| CN | 111566854 A | 8/2020 |
| DE | 102005044360 A1 | 3/2007 |
| EP | 2140958 A2 | 1/2010 |
| EP | 2559436 A1 | 2/2013 |
| EP | 3197622 A1 | 8/2017 |
| GB | 2442051 A | 3/2008 |
| JP | 54-069726 A | 6/1979 |
| JP | 11-126634 A | 5/1999 |
| JP | 2006-351465 A | 12/2006 |
| JP | 2007-109618 A | 4/2007 |
| JP | 2008-527169 | 7/2008 |
| JP | 2010-001528 A | 1/2010 |
| KR | 2006-0021749 A | 3/2006 |
| WO | 2005/027255 A1 | 3/2005 |
| WO | 2005/094501 A2 | 10/2005 |
| WO | 2006/026026 A2 | 3/2006 |
| WO | 2006/053225 A2 | 5/2006 |
| WO | 2006/062826 A2 | 6/2006 |
| WO | 2006/126823 A1 | 11/2006 |
| WO | 2008/043396 A1 | 4/2008 |
| WO | 2008/153239 A1 | 12/2008 |
| WO | 2009/025955 A1 | 2/2009 |
| WO | 2009/044146 A1 | 4/2009 |
| WO | 2009/046081 A2 | 4/2009 |
| WO | 2009/066011 A2 | 5/2009 |
| WO | 2009/091900 A1 | 7/2009 |
| WO | 2011/045627 A1 | 4/2011 |
| WO | 2012/082364 A1 | 6/2012 |
| WO | 2013/006430 A2 | 1/2013 |
| WO | 2013/141879 A1 | 9/2013 |
| WO | 2014/066850 A2 | 5/2014 |
| WO | 2014/096556 A2 | 6/2014 |
| WO | 2014/137352 A1 | 9/2014 |
| WO | 2014/190097 A1 | 11/2014 |
| WO | 2016/007112 A1 | 1/2016 |
| WO | 2016/007113 A1 | 1/2016 |
| WO | 2016/049132 A1 | 3/2016 |

OTHER PUBLICATIONS

Prabhu, S, et al. "Silver nanoparticles: mechanism of antimicrobial action, synthesis, medical applications, and toxicity effects" International Nano Letters 2012, 2:32 (Year: 2012).*

Naftulin (https://www.sciencealert.com/a-deadly-fungus-is-spreading-across-the-world-and-we-don-t-know-how-to-stop-it) Apr. 9, 2019, pp. 1-4 (Year: 2019).*

CDC "Marburg Virus Disease" (https://www.cdc.gov/marburg/about/index.html) May 1, 2024, pp. 1-5 (Year: 2024).*

Ding et al. (CN 108091834 A Espacenet machine translation, 2018 (Year: 2018).

Phuoc et al, "Synthesis of Ag-deoionized water nanofluids using multi-beam laser ablation in fluids", Optics and Lasers in Engineering 45 (2007) 1099-1106.

Prabhu et al., "Silver nanoparticles: mechanism of antimicrobial action, synthesis, medical applications, and toxicity effects", International Nano Letters, 2012, 2:32, pp. 1-10.

Rawashdeh et al., "Antibacterial Mechanisms of Metallic Nanoparticles: A Review", Dynamic Biochemistry, Process Biotechnology and Molecular Biology 2009 pp. 12-20.

Rhim, J.-W. et al. "Preparation and characterization of bio-nanocomposite films of agarand silver nanoparticles: Laser ablation method" Carbohydrate Polymers 103 (2014) 456-465 (Year: 2014).

Riabinina et al., "Influence of pressure on the Pt nanoparticle growth modes during pulsed laser ablation", Journal of Applied Physics 108, 034322 (2010, published online Aug. 12, 2010).

Samberg et al. (Nanotoxicology 2011 ;5(2):244-253) (Year: 2011).

Santos et al., "Enhancement of antibiotic effect via gold:silver-alloy nanoparticles", J. Nanopart Res (2012) 14:859, pp. 1-8.

Sweeney et al., "Rapid Purification and Size Separation of Gold Nanoparticles via Diafiltration", J. Am. Chem. Soc. 2006, 128, 3190-3197 (Published on web Feb. 18, 2006).

Sylvestre et al., "Surface Chemistry of Gold Nanoparticles Produced by Laser Ablation in Aqueous Media", J Phys. Chem. B 2004, 108, 16864-16869.

Thanaa Majied Al-Nori, "Antibacterial activity of Silver and Gold Nanoparticles against *Streptococus, Staphylococcus aureus* and *E.coli*", Al-Mustansiriya J. Sci, Vo. 23, No. 3, 2012.

Theodorou et al., "Inhalation of Silver Nanomaterials—Seeing the Risks", International Journal of Molecular Sciences, 2014, 15, 23936-23974.

Tu et al. "Nanoporous Polymer-Ceramic Composite Electrolytes for Lithium Metal Batteries", Adv. Energy Mater., 2014; 4: 1300654.

U.S. Appl. filed Apr. 1, 2016, Tarbet et al., U.S. Appl. No. 15/088,863.

U.S. Appl. filed Apr. 13, 2016, Tarrbet et al., U.S. Appl. No. 15/098,071.

U.S. Appl. filed Jan. 25, 2017, Niedermeyer., U.S. Appl. No. 15/415,562.

U.S. Appl. filed Jun. 19, 2018, Niedermeyer., U.S. Appl. No. 16/012,508.

U.S. Appl. filed Jun. 6, 2014, Neidermeyer., U.S. Appl. No. 14/298,593.

U.S. Appl. filed Jun. 6, 2014, Neidermeyer., U.S. Appl. No. 14/298,594.

U.S. Appl. filed Jun. 6, 2014, Neidermeyer., U.S. Appl. No. 14/298,598.

U.S. Appl. filed May 10, 2018, Niedermeyer., U.S. Appl. No. 15/976,447.

U.S. Appl. filed Nov. 29, 2017, Tarbet et al., U.S. Appl. No. 15/829,512.

U.S. Appl. filed Nov. 9, 2017, Niedermeyer., U.S. Appl. No. 15/808,088.

U.S. Appl. filed Sep. 22, 2015, Neidermeyer., U.S. Appl. No. 14/861,243.

U.S. Appl. filed Sep. 22, 2015, Neidermeyer., U.S. Appl. No. 14/861,318.

U.S. Appl. filed Sep. 22, 2015, Neidermeyer., U.S. Appl. No. 14/861,375.

U.S. Appl. filed Sep. 22, 2015, Neidermeyer., U.S. Appl. No. 14/861,442.

U.S. Appl. filed Sep. 22, 2015, Neidermeyer., U.S. Appl. No. 14/861,500.

U.S. Appl. filed Sep. 22, 2015, Neidermeyer., U.S. Appl. No. 14/861,562.

U.S. Appl. No. 15/098,071, filed Apr. 13, 2016, Tarbet et al.

U.S. Application Filed on Jun. 19, 2018, by Niedermeyer, U.S. Appl. No. 16/012,508.

U.S. Application Filed on Nov. 27, 2018, by Niedermeyer, U.S. Appl. No. 16/202,078.

U.S. Patent Application filed on Apr. 1, 2016, by Tarbet et al., U.S. Appl. No. 15/088,863.

U.S. Patent Application filed on Jan. 25, 2017, by Niedermeyer, U.S. Appl. No. 15/415,562.

U.S. Patent Application Filed on Jun. 6, 2014, by Neidermeyer, U.S. Appl. No. 14/298,594.

U.S. Patent Application Filed on Sep. 22, 2015, by Neidermeyer, U.S. Appl. No. 14/861,375.

U.S. Patent Application Filed on Sep. 22, 2015, by Neidermeyer, U.S. Appl. No. 14/861,442.

Xiang Dongxi, "Study of Silver-nanoparticles on antiviral action", Journal of Dalian Medical University, vol. 31, No. 6, 2009.

Xinxia Yue, et al., "Preparation of silver nanoparticles by tea extracts and its application in the antibacterial finishing of cotton fabric", 2014, Shanghai Textile Science & Technology, vol. 42, No. 5, p. 45-49.

Yuteng Wan et al., "Modification of coral-like SnO2 nanostructures with dense TiO2 nanoparticles for a self-cleaning gas sensor", Talanta, vol. 99, pp. 394-403.

"International Coral Reef Initiative,""What are Corals"", downloaded from http://www.iciforum.org/about-on Sep. 5, 2017."

(56) References Cited

OTHER PUBLICATIONS

Agnihotri, Shekar, et al., "Immobilized silver nanoparticles enhance contact killing and show highest efficacy: elucidation of the mechanism of bacterial action of silver," Nanoscale, 2013. published Jan. 3, 2013. (Year: 2013).

Badawy et al., "Surface Charge-Dependent Toxicity of Silver Nanoparticles", Environ. Sci. Technol. 2011, 45, 283-287.

Barcikowski et al., "Generation of nanoparticle colloids by picosecond and femtosecond laser ablations in liquid flow", Appl. Phys. Lett. 91, 083113 (2007).

Chien et al., "Synthesis of nanoparticles: sunlight formation of gold nanodecahedra for ultra-sensitive lead-ion detection", Green Chem., vol. 13, pp. 1162-1166, May 2011.

Choudhury et al. "A highly reversible room-temperature lithium metal battery based on crosslinked hairy nanoparticles", Nature Communications, 2015; DOI: 10.1038/ncomms10101.

Correard et al.,"Gold nanoparticles prepared by laser ablation in aqueous biocompatible solutions: assessment of safety and biological identity for nanomedicine applications", International Journal of Nanomedicine, Nov. 21, 2014; pp. 5415-5430.

Cox (https://microbiologysociety.org/blog/rabies-virus-can-we-treat-the-untreatable.html) Jun. 25, 2019, pp. 1-4 (Year: 2019).

Daissy Paredes, et al., "Synthesis, characterization, and evaluation of antibacterial effect of Ag nanoparticles against *Escherichia coli* 0157:h7 and methicillin-resistant *Staphylococcus aureus* (Mrsa)", Apr. 3, 2014, International Journal of Nanomedicine, p. 1717-1729.

Examiner Interview Summary received for U.S. Appl. No. 16/202,078, mailed on Nov. 6, 2020, 3 pages.

Gogoi et al. (Langmuir 2006;22:9322-9328) (Year: 2006).

Guangnian Xu, et al."Progress in preparation of nano-silver", 2019, Materials Review, vol. 24, No. 11, p. 139-142.

Gui, M. et al. "Cryo-electron microscopy structures of the SARS-CoV spike glycoprotein reveal a prerequisite conformational state for receptor binding" Cell Research (2017) 27:119-129 (Year: 2017).

Gurevitch et al. "Nanocomposites of Titanium Dioxide and Polystyrene-Poly(ethylene oxide) Block Copolymer as Solid- State Electrolytes for Lithium Metal Batteries", Journal of the Electrochemical Society, 2013; 160(9): A1611-A1617.

Hamada et al., Espacenet machine translation for JP 2006-351465 A (Year: 2006).

Hamm et al. "Ionic conductivity enhancement of sputtered gold nanoparticle-in-ionic liquid electrolytes", J Mater Chem A, 2014; 2(3): 792-803.

He et al. "Ionic liquid and nanoparticle hybrid systems: Emerging applications", 2017. Advances in Colloid and Interface Science, 2017; 244: 54-70.

Hopp Bela et al, "Production of nanostructures on bulk metal samples by laser ablation for fabrication of low-reflective surfaces", applied physics a materials science & processing, Springer Berlin Heidelberg, vol. 113, No. 2, Aug. 14, 2013, pp. 291-296.

Hultin, "A Guide to Solvents and Reagents in Introductory Organic Chemistry for students in 2.222", Obtained from https://home.cc. umanitoba.ca/hultin/chem2220/Support/solvents_and_reagent- s.pdf on Jan. 25, 2018, originally published Feb. 12, 2002—17 pages.

International Coral Reef Initiative, "What are Corals", downloaded from http://www.iciforum.org/about-coral-reefs/what-are-corals on Sep. 5, 2017.

International Search Report and Written Opinion received for PCT Patent Application No. PCT/US2020/041796, mailed on Oct. 7, 2020, 9 pages.

International Search Report and Written Opinion received for PCT Patent Application No. PCT/US22/71448, mailed on Jun. 7, 2022, 9 pages.

International Search Report cited in PCT/US18/62864 dated Nov. 28, 2018.

International Search Report for PCT App. No. PCT/US2012/044907 dated Jan. 31, 2013.

International Search Report for PCT App. No. PCT/US2015/051638 dated Jan. 29, 2016.

International Search Report for PCT App. No. PCT/US2015/051639 dated Dec. 17, 2015.

International Search Report for PCT App. No. PCT/US2015/051640 dated Dec. 17, 2015.

International Search Report for PCT App. No. PCT/US2015/051642 dated Dec. 14, 2015.

International Search Report for PCT App. No. PCT/US2015/051643 dated Dec. 17, 2015.

International Search Report for PCT App. No. PCT/US2015/051646 dated Dec. 18, 2015.

International Search Report for PCT App. No. PCT/US2015/051649 dated Dec. 17, 2015.

Jacobson, "These six diseases should worry you more than Ebola", Inside Energy Oct. 2014; [online] retrieved on Jan. 29, 2017 from http://www.pbs.org/newshour/updates/six-diseases-actually-worry/; 10 pages.

Jacobson, R. Inside Energy Oct. 2014; [online] retrieved on Jan. 29, 2017 from: http://www.pbs.org/newshour/updates/six-diseases-actually-worry/; 10 pages.

Jana et al., "Seeding Growth for Size Control of 5-40 nm Diameter Gold Nanoparticles", Langmuir 2001, 17, 6782-6786.

Kewal K. Jain MD, FRACS, FFPM., "The Handbook of Nanomedicine" Humana Press, 2008.

Korf et al. "Piperidine tethered nanoparticle-hybrid electrolyte for lithium metal batteries", J Mater. Chem., 2014; 2: 11866-11873.

Kozawa et al., Espacenet machine translation for JP 2007-109618A (Year: 2007).

Leisure Pro, "Coral Identification: Types of Coral (Part 1—Hard Coral)", downloaded from http://www.leisurepro.com/blog/explorethe- blue/coral-identification-types-of-coral-part-1 on Sep. 2017.

Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.

Lu et al. "Ionic-Liquid-Nanoparticle Hybrid Electrolytes: Applications in Lithium Metal Batteries", Angew. Chem. Int. Ed., 2014; 53: 488-492.

Mafune et al., "Formation of Stable Platinum Nanoparticles by Laser Ablation in Water", J. Phys. Chem. B 2003, 107, 4218-4223.

Malvern, "The use of the Malvern Zetasizer for the measurement of Zeta Potential", article from the Internet, http://www.malvern.co.alLaboratory/zetaintm.htm> 10 pages, printed on Feb. 12, 2002.

Malvern, "Zeta Potential Theory, Dispersion stability", article from the Internet, http://www.malvern.co.uk/Laboratory/zettheo.htm >, 3 pages, printed on Feb. 12, 2002.

Muller, M. "Bacterial Silver Resistance Gained by Cooperative Interspecies Redox Behavior" Antimicrobial Agents and Chemotherapy 2018, 62 (8), 1-10 (Year: 2018).

Mycozil, "The Benefits of Colloidal Silver for Toenail Fungus", http://www.nailfungustoenail.com/benefitsofcol-loidalsilverfortoenailfungu- s.html.

Nakashima et al. "Preparation of fusion materials based on ionic liquids and cationic gold nanoparticles", Polymer Journal, 2015; 47: 171-176.

NOAA Ocean Service Education, "Corals", downloaded from https://oceanservice.noaa.gov/education/kits/corals/coral03_growth.html on Sep. 5, 2017.

Pal et al., "Does the Antibacterial Activity of Silver Nanoparticles Depend on the Shape of the Nanoparticle?", Applied and Environmental Microbiology, 2007; 73(6): 1712-1720.

Pan et al. "Hybrid Electrolytes with Controlled Network Structures for Lithium Metal Batteries", Adv. Mater., 2015; 27: 5995-6001.

International Preliminary Report on Patentability received for PCT Patent Application No. PCT/US15/051643, mailed on Apr. 6, 2017, 7 pages.

International Preliminary Report on Patentability received for PCT Patent Application No. PCT/US2018/062864, mailed on Jun. 11, 2020, 8 pages.

International Preliminary Report on Patentability received for PCT Patent Application No. PCT/US22/71448, mailed on Oct. 12, 2023, 6 pages.

(56)          References Cited

OTHER PUBLICATIONS

International Search Report and Written Opinion received for PCT Patent Application No. PCT/US15/051643, mailed on Dec. 17, 2015, 8 pages.

International Search Report and Written Opinion received for PCT Patent Application No. PCT/US2018/062864, mailed on Feb. 8, 2019, 14 pages.

Ding et al., CN 108091834; Espacenet machine translation, 2018 (Year: 2018).

Xu et al., "Comparison of sizing small particles using different technologies", Powder Technology, vol. 132, Feb. 10, 2003, pp. 145-153.

Yeh C-H. et al., "Physical and electrochemical characterization of PbO2 electrode prepared at different H2S04/H20/Pb0 ratios", Journal of Power Sources IOI, Jan. 31, 2001, pp. 219-225.

* cited by examiner 20 nm

ANTIMICROBIAL COMPOSITIONS AND METHODS

CROSS-REFERENCE TO RELATED APPLICATIONS

This application is a continuation-in-part of U.S. patent application Ser. No. 16/012,508, filed Jun. 19, 2018, which is a division of U.S. patent application Ser. No. 14/861,243, filed Sep. 22, 2015, which claims the benefit of U.S. Provisional Patent Application No. 62/054,152, filed Sep. 23, 2014, and U.S. Provisional Patent Application No. 62/054,154, filed Sep. 23, 2014. Each of the foregoing is incorporated herein by reference in its entirety.

BACKGROUND

1. Field of the Invention

Disclosed herein are antimicrobial compositions and methods for killing microbes using such compositions.

2. Relevant Technology

Diseases old and new caused by microbes such as bacteria, viruses, and fungi continue to plague humans, animals, and plants. In addition to infecting humans, sometimes as epidemics or pandemics, microbial diseases that affect animals and plants raised for food have and can continue to devastate food supplies. Food products are also prone to spoilage as a result of microbes, particularly bacteria and fungi.

Although modern science has yielded many new antimicrobial compositions, some, such as antibiotics, are not always effective because microbes can build up tolerance or immunity to such compositions. In addition, apart from natural immunity and acquired immunity from vaccinations, there are no compositions that can reliably target and selectively destroy viruses.

Besides specific compositions and drugs, there are non-specific ways to combat microbes and microbial diseases, such as burning, harsh chemicals, and partial or complete removal of diseased human, animal, or plant tissues. Because such measures are non-specific and often kill or severely affect the organism being treated, they are usually used as a last resort.

Among the deadliest human diseases are anthrax, caused by *Bacillus anthracis*; ebola virus disease; hemorrhagic fever, caused by Marburg virus; hantavirus; rabies; smallpox; Crimean-Congo hemorrhagic, fever caused by a tick-borne virus; avian influenza (bird flu); severe acute respiratory syndrome (SARS), caused by coronavirus; malaria, caused by mosquitos infected with Plasmodium parasites; typhoid fever caused by *Salmanella typhi* bacterium; cholera, an acute intestinal infection caused by Vibrio cholera bacterium; yellow fever, a hemorrhagic fever transmitted by infected mosquitoes; acquired immune deficiency syndrome (AIDS); bubonic plague, caused by *Yersinia pestis* bacterium; and wound and flesh infections caused by many different bacteria, particularly those which are antibiotic-resistant.

There are also many plant diseases of many types that could threaten the world's food supply. An example of a potentially devastating plant disease is citrus greening disease, which affects citrus trees and for which there is no cure. Citrus greening disease is caused by motile bacteria, *Candidatus liberibacter* spp. and transmitted by insects (e.g., various types of psyllids). In the heyday of Florida citrus, around 1970, the number of acres with orange, grapefruit, and specialty fruit orchards surpassed 900,000. Today, it is reportedly slightly more than 500,000 acres as a result of citrus greening disease.

Botulism from consuming spoiled food is a relatively rare but serious and potentially fatal paralytic illness caused by a nerve toxin that is produced by the bacterium *Clostridium botulinum.*

Among the deadliest viral diseases is Ebola disease, with a mortality rate that is reportedly as high as 90%. Ebola virus disease (EVD), Ebola hemorrhagic fever (EHF), or simply Ebola is a disease of humans and other primates caused by an Ebola virus. Symptoms of the disease can start two days to three weeks after contracting the virus, with a fever, sore throat, muscle pain and headaches. Typically, vomiting, diarrhea and rash follow, along with decreased functioning of the liver and kidneys. Around this time, affected people may begin to bleed both within the body and externally.

EVD is caused by four of five viruses classified in the genus *Ebolavirus*, family Filoviridae, order Mononegavirales. The four disease-causing viruses are Bundibugyo virus (BDBV), Sudan virus (SUDV), Taï Forest virus (TAFV), and one called simply, Ebola virus (EBOV, formerly Zaire Ebola virus). Ebola virus is the sole member of the Zaire *ebolavirus* species, and the most dangerous of the known Ebola disease-causing viruses, as well as being responsible for the largest number of outbreaks. The fifth virus, Reston virus (RESTV), is not thought to be disease-causing in humans. The five Ebola viruses are closely related to Marburg viruses.

No specific treatment for EVD is yet available. Efforts to help those who are infected are supportive and include giving either oral rehydration therapy or intravenous fluids. EVD has a high risk of death, killing between 50% and 90% of those infected. EVD was first identified in Sudan (now South Sudan) and the Democratic Republic of the Congo. Efforts are under way to develop a vaccine; however, none yet exists.

Accordingly, there has been and remains a need to find compositions that can reliably target and preferentially kill or deactivate disease-causing microbes without killing or causing undue harm to the organism being treated (e.g., human, animal, or plant).

SUMMARY

Disclosed herein are antimicrobial compositions and methods for killing or deactivating a wide variety of harmful microbes, such as viruses, bacteria, and fungi, which can infect humans, animals, plants, or food supplies. Also disclosed are methods for making antimicrobial compositions. Unexpectedly, it has now been found that by selecting metal nanoparticles of a particular size and particle size distribution it is possible to target and preferentially kill or deactivate a specific type of microbe.

In some embodiments, an antimicrobial composition may comprise (1) a carrier and (2) a plurality of metal nanoparticles having a particle size and a particle size distribution selected so as to selectively and preferentially kill one of a virus, bacterium, or fungus.

In some embodiments, anti-viral compositions can include metal nanoparticles having a particle size of about 8 nm or less, or about 1 nm to about 7 nm, or about 2 nm to about 6.5 nm, or about 3 nm to about 6 nm. Within these size ranges it is possible to select "designer anti-viral particles" of specific size that are particularly effective in targeting a specific virus.

In some embodiments, an anti-viral composition may comprise a plurality of non-ionic metal nanoparticles having a particle size in a range of about 0.22 nm to about 2 nm, or about 0.22 nm to about 1.5 nm, or about 0.24 nm to about 1 nm, or about 0.27 nm to about 0.7 nm, or about 0.3 nm to about 0.5 nm, or about 0.35 nm to about 0.45 nm. For example, such embodiments may be useful for targeting and preferentially deactivating Ebola viruses.

In some embodiments, anti-viral compositions can include metal nanoparticles having a particle size of about 2 nm to about 10 nm, or about 4 nm to about 10 nm, or about 6 nm to about 10 nm. For example, such embodiments with particles that are 6 nm, 10 nm, or both may be useful for targeting and preferentially deactivating Ebola viruses by associating with, binding to, and/or disrupting the 3CSY glycoprotein found on the surface of Ebola viruses, thereby preventing binding of the virus to cell surface receptors.

In some embodiments, anti-bacterial compositions can include metal nanoparticles having a particle size of about 3 nm to about 14 nm, or about 5 nm to about 13 nm, or about 7 nm to about 12 nm, or about 8 nm to about 10 nm. Within these size ranges it is possible to select "designer anti-bacterial particles" of specific size that are particularly effective in targeting a specific bacterium.

In some embodiments, anti-fungal compositions can include metal nanoparticles having a particle size of about 9 nm to about 20 nm, or about 10 nm to about 18 nm, or about 11 nm to about 16 nm, or about 12 nm to about 15 nm. Within these size ranges it is possible to select "designer anti-fungal particles" of specific size that are particularly effective in targeting a specific fungus.

In some embodiments, metal nanoparticles can comprise spherical-shaped metal nanoparticles having a mean diameter and a particle size distribution wherein at least 99% of the metal nanoparticles have a particle size within 30% of the mean diameter, or within 20% of the mean diameter, or within 10% of the mean diameter and/or wherein at least 99% of the spherical-shaped nanoparticles have a diameter within ±3 nm of the mean diameter, or within ±2 nm of the mean diameter, or within ±1 nm of the mean diameter.

In some embodiments, metal nanoparticles can comprise coral-shaped metal nanoparticles having a non-uniform cross section and a globular structure formed by multiple, non-linear strands joined together without right angles. In some cases the coral-shaped metal nanoparticles can be used together with spherical-shaped metal nanoparticles (e.g., in order to potentiate the spherical-shaped metal nanoparticles).

In some embodiments, metal nanoparticles can comprises at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof. Nanoparticles comprised of silver, gold, and mixtures and alloys thereof can be particularly effective.

In some embodiments, a method of killing or deactivating a microbe comprises: (1) applying an antimicrobial composition comprising a carrier and metal nanoparticles onto or into a substrate containing microbes, and (2) the antimicrobial composition killing or deactivating the microbes. The substrate can be a living organism or a non-living object.

In some embodiments, a method of deactivating a virus comprises: (1) applying an anti-viral composition comprising metal nanoparticles having a particle size of about 8 nm or less, or about 1 nm to about 7 nm, or about 2 nm to about 6.5 nm, or about 3 nm to about 6 nm onto or into a substrate containing a virus, and (2) the anti-viral composition deactivating the virus.

In some embodiments, a method of deactivating Ebola viruses comprises: (1) applying an anti-viral composition comprising a carrier and metal nanoparticles onto or into an animal or non-living substrate contaminated with Ebola viruses, and (2) the metal nanoparticles deactivating Ebola viruses by attaching to glycoproteins and/or denaturing one or more proteins in the Ebola viruses.

In some embodiments, a method of treating or preventing Ebola virus disease comprises: (1) administering a pharmaceutically acceptable quantity of spherical-shaped nonionic metal nanoparticles having a particle size in a range of about 0.22 nm to about 2 nm to a living organism; and (2) the spherical-shaped nonionic metal nanoparticles deactivating Ebola viruses on or in the living organism.

In some embodiments, a method of treating or preventing Ebola virus disease comprises: (1) administering a pharmaceutically acceptable quantity of spherical-shaped nonionic metal nanoparticles having a particle size in a range of about 2 nm to about 10 nm to a living organism; and (2) the spherical-shaped nonionic metal nanoparticles deactivating Ebola viruses on or in the living organism by binding to, associating with, and/or disrupting the 3CSY glycoproteins of the Ebola viruses.

In some embodiments, a method of killing a bacterium comprises: (1) applying an anti-bacterial composition comprising metal nanoparticles having a particle size of about 8 nm or less, or about 3 nm to about 14 nm, or about 5 nm to about 13 nm, or about 7 nm to about 12 nm, or about 8 nm to about 10 nm onto or into a substrate containing a bacterium, and (2) the anti-bacterial composition killing the bacterium.

In some embodiments, a method of killing a fungus comprises: (1) applying an anti-fungal composition comprising metal nanoparticles having a particle size of about 9 nm to about 20 nm, or about 10 nm to about 18 nm, or about 11 nm to about 16 nm, or about 12 nm to about 15 nm onto or into a substrate containing a fungus, and (2) the anti-fungal composition killing the fungus.

These and other advantages and features of the invention will be set forth in part in the description which follows, and in part will become apparent to those skilled in the art upon examination of the following or may be learned by practice of the invention.

DETAILED DESCRIPTION

Figure 1A:
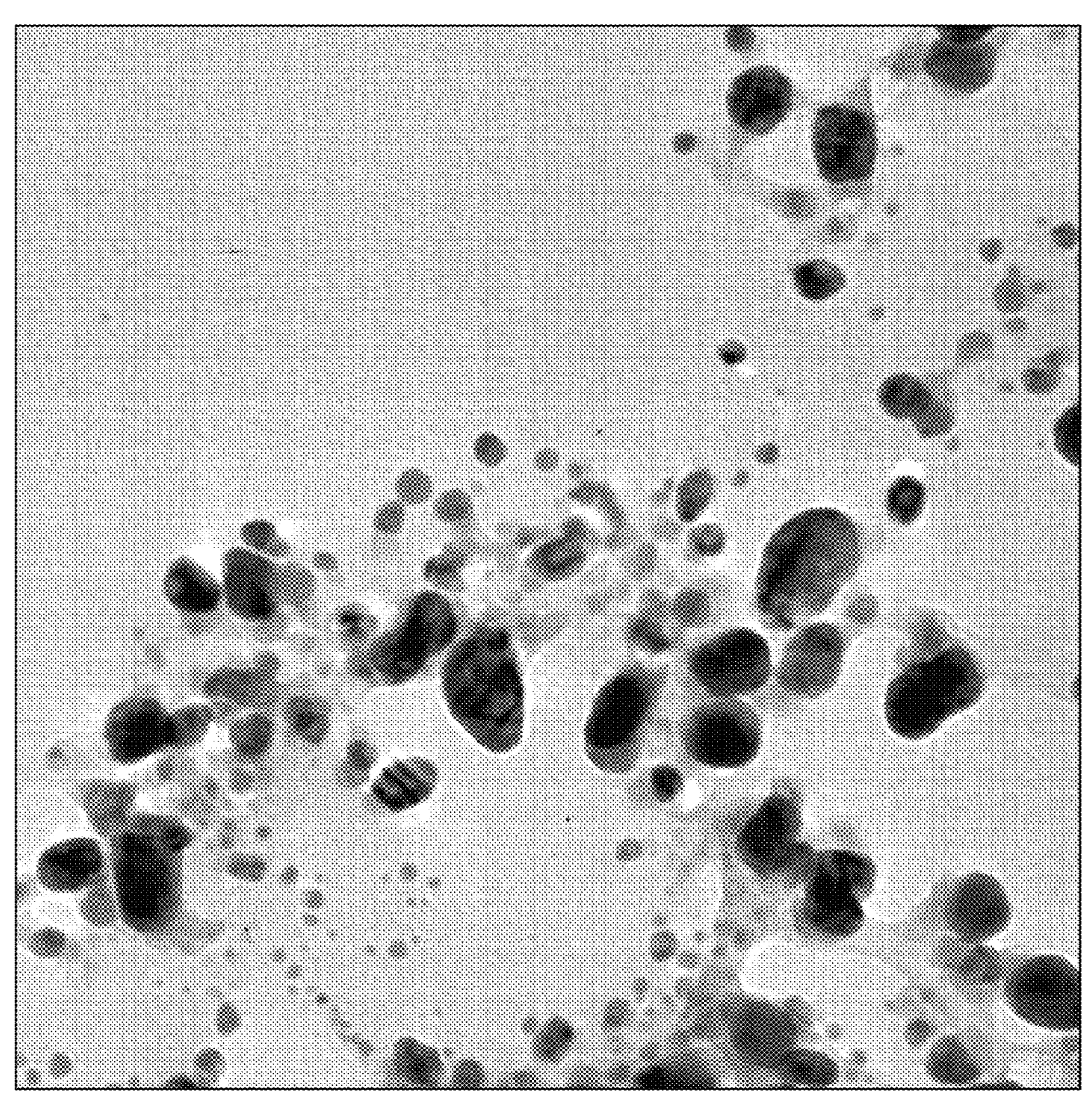
FIGS. 1A-1D show TEM images of various non-spherical nanoparticles (i.e., that have surface edges and external bond angles) made according to conventional chemical synthesis or electrical discharge methods.

Disclosed herein are antimicrobial compositions and methods for killing or deactivating microbes, such as viruses (including Ebola viruses), bacteria, or fungi. In some embodiments, metal nanoparticles are dispersed within or contained on or within a carrier that can be applied onto or into a substrate containing a microbe. The carrier can be a liquid, gel or solid. The antimicrobial compositions can be formulated to selectively and preferentially kill one or more specific microbes.

In some embodiments, antimicrobial compositions may comprise a carrier and a plurality of metal nanoparticles having a particle size and a particle size distribution selected so as to selectively and preferentially kill one of a virus, a bacterium, or a fungus.

In some embodiments, anti-viral compositions comprise metal nanoparticles having a particle size of about 8 nm or less, or about 0.22 nm to about 2 nm, or about 0.22 nm to about 1.5 nm, or about 0.24 nm to about 1 nm, or about 0.27 nm to about 0.7 nm, or about 0.3 nm to about 0.5 nm, or about 0.35 nm to about 0.45 nm, or about 1 nm to about 7 nm, or about 2 nm to about 6.5 nm, or about 3 nm to about 6 nm, or about 2 nm to about 10 nm, or about 4 nm to about 10 nm, or about 6 nm to about 10 nm.

In some embodiments, anti-bacterial compositions can include metal nanoparticles having a particle size of about 3 nm to about 14 nm, or about 5 nm to about 13 nm, or about 7 nm to about 12 nm, or about 8 nm to about 10 nm.

In some embodiments, anti-fungal compositions can include metal nanoparticles having a particle size of about 9 nm to about 20 nm, or about 10 nm to about 18 nm, or about 11 nm to about 16 nm, or about 12 nm to about 15 nm.

Within any of the foregoing size ranges, it is possible to select "designer antimicrobial particles" of specific size that are particularly effective in targeting a specific microbe.

The ability to select and use microbe-specific nanoparticles provides a number of benefits. In the case where only certain nanoparticle sizes are effective in killing a particular microbe or class of microbes, providing metal nanoparticles within a narrow particle size distribution of the correct particle size maximizes the proportion of nanoparticles that are effective in killing the target microbe and minimizes the proportion of nanoparticles that are less effective, or ineffective, in killing the target microbe. This, in turn, greatly reduces the overall amount or concentration of nanoparticles required to provide a desired kill- or deactivation rate of a targeted microbe. Eliminating improperly-sized nanoparticles also reduces the tendency of the composition to kill or harm non-targeted microbes or other cells, such as healthy mammalian or human cells. In this way, highly specific antimicrobial compositions can better target a harmful microbe while being less harmful or even non-toxic to humans, animals, and plants.

Nanoparticle Configurations

In some embodiments, the metal nanoparticles may comprise or consist essentially of nonionic, ground state metal nanoparticles. Examples include spherical-shaped metal nanoparticles, coral-shaped metal nanoparticles, or a blend of spherical-shaped metal nanoparticles and coral-shaped metal nanoparticles.

In some embodiments, nonionic metal nanoparticles useful for making antimicrobial compositions comprise spherical nanoparticles, preferably spherical-shaped metal nanoparticles having a solid core. The term "spherical-shaped metal nanoparticles" refers to nanoparticles that are made from one or more metals, preferably nonionic, ground state metals, having only internal bond angles and no external edges or bond angles.

This is in contrast to hedron-like, faceted, or crystalline nanoparticles, which are often formed using conventional chemical synthesis methods, even though such nanoparticles are often erroneously described in the art as being "spherical" in shape. The skilled person will thus understand that "spherical" nanoparticles as used herein are formed from a laser ablation process that results in nanoparticles of different morphology and functionality as compared to nanoparticles formed via another process such as chemical synthesis, even if such nanoparticles are erroneously described as "spherical." Moreover, preferred nanoparticles disclosed herein, including spherical nanoparticles, omit coating agents or capping agents that are frequently required in other nanoparticle systems to halt particle growth and/or prevent agglomeration.

In this way, the spherical nanoparticles are highly resistant to ionization, highly stable, and highly resistance to agglomeration. Such nanoparticles can exhibit a high $\xi$-potential, which permits the spherical nanoparticles to remain dispersed within a polar solvent without a surfactant, which is a surprising and unexpected result.

In general, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. Nevertheless, selecting spherical-shaped nanoparticles of specific particle size and narrow particle size distribution can be particularly useful for selectively and preferentially killing or deactivating a particular type of microbe, such as a virus, bacterium, or fungus.

In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a $\xi$-potential of at least 10 mV, preferably at least about 15 mV, more preferably at least about 20 mV, even more preferably at least about 25 mV, and most preferably at least about 30 mV.

The "mean diameter" can be determined using methods known to those of skill in the art, including via laser diffraction (e.g., dynamic light scattering) methods, acoustic spectroscopy methods (e.g., Coulter counter), or microscopy techniques (e.g., TEM, SEM). The mean diameter can represent the De Brouckere mean diameter (i.e., mean diameter weighted by particle volume), the Sauter mean diameter (i.e., normalized by volume/surface area ratio), the arithmetic mean, or surface area mean, for example.

Examples of methods and systems for manufacturing spherical-shaped nanoparticles are disclosed in U.S. Pat. No. 9,849,512 to William Niedermeyer, incorporated herein by reference.

Figure 1B:
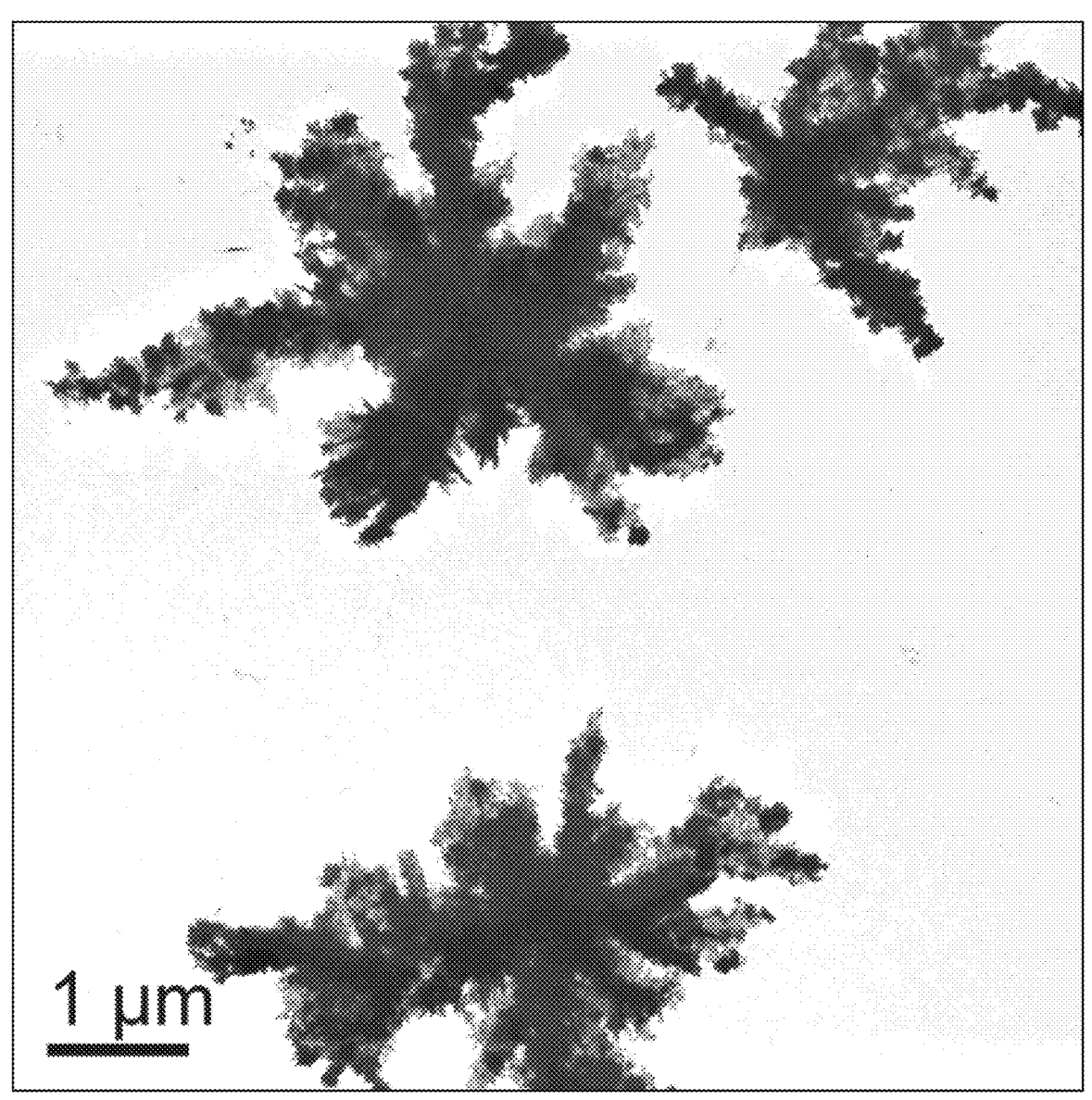
Figure 1C:
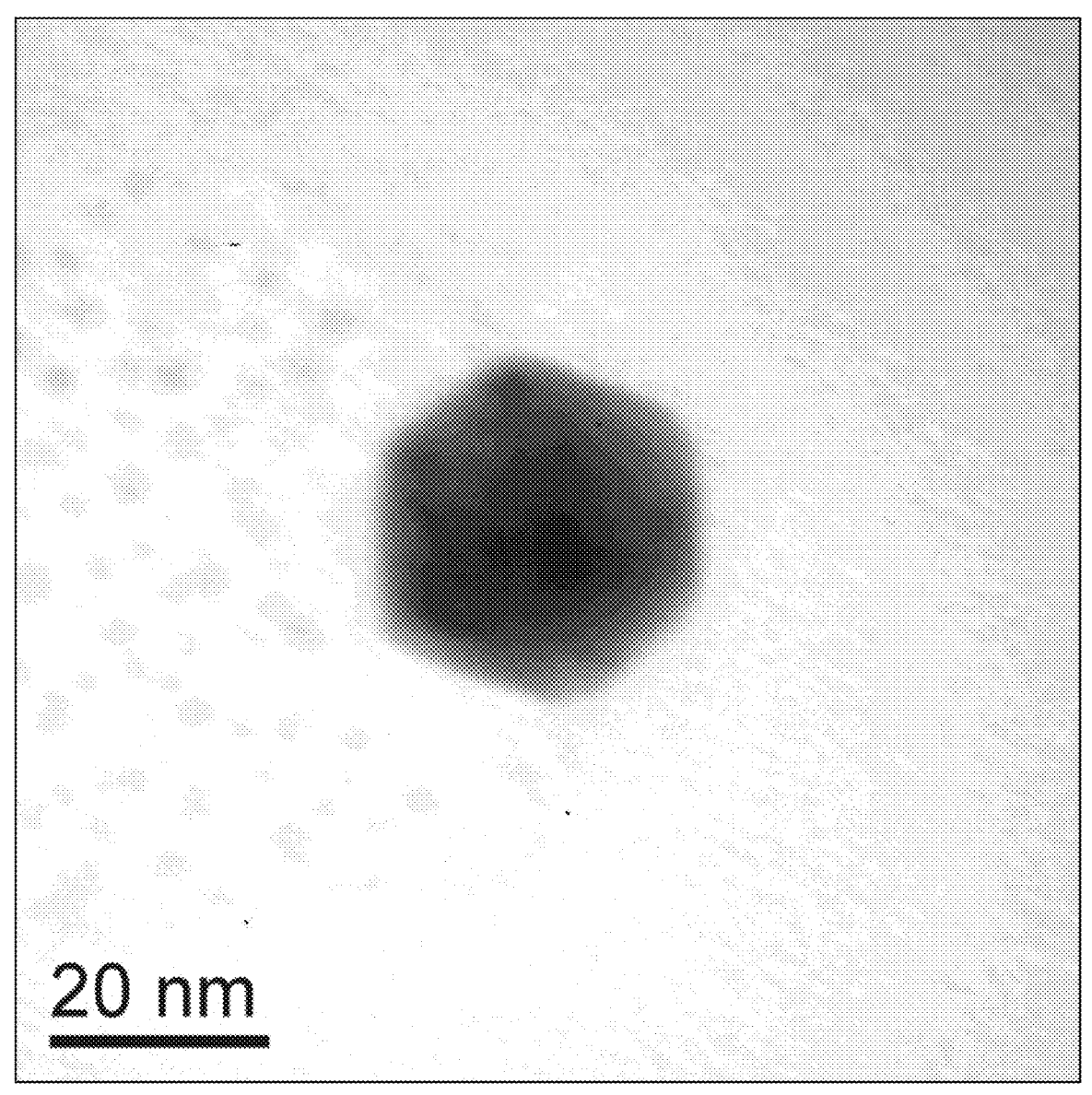
Figure 1D:
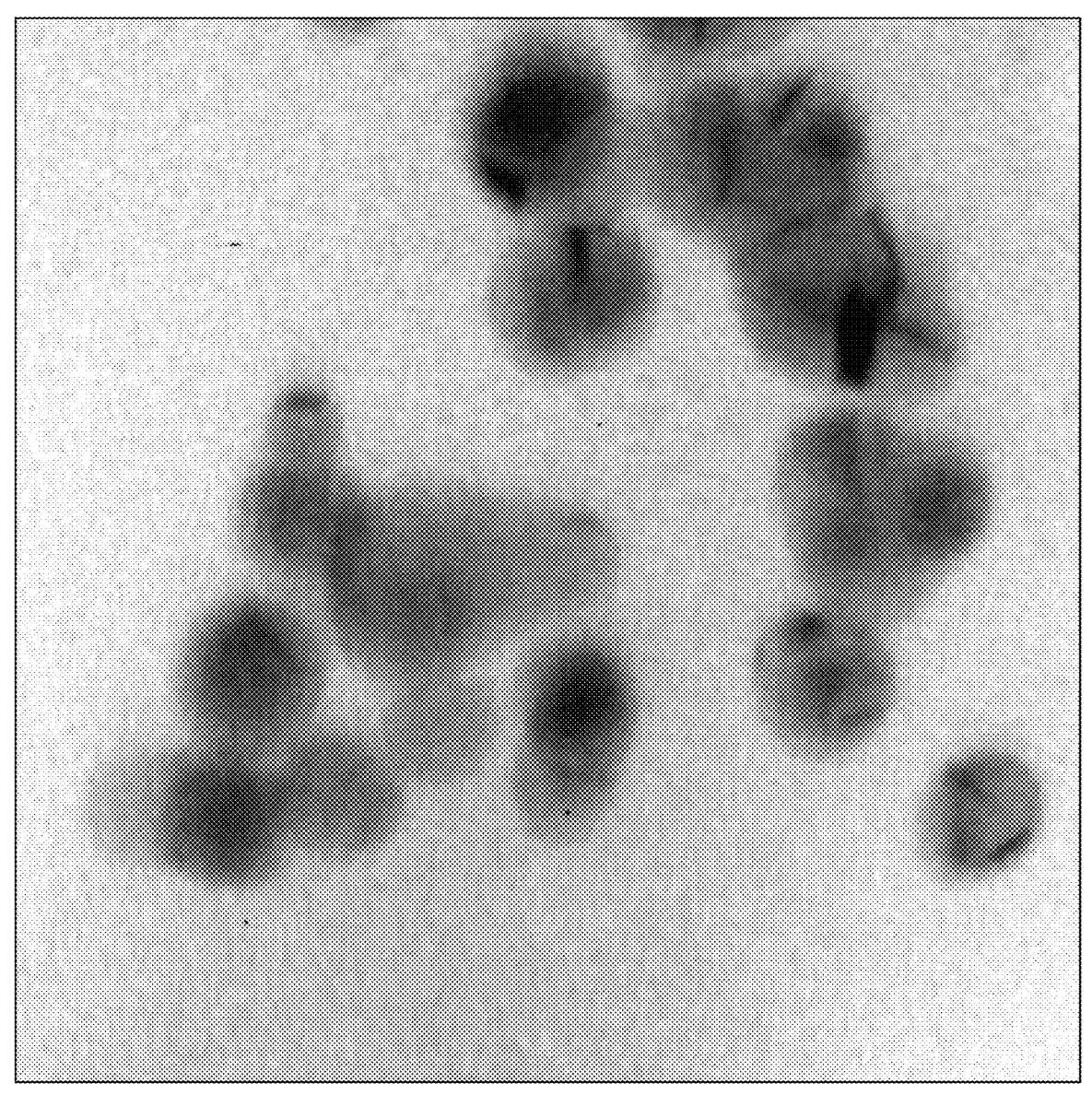

FIGS. 1A-1D show transmission electron microscope (TEM) images of nanoparticles made according to various chemical synthesis methods. As shown, the nanoparticles formed using these various chemical synthesis methods tend to exhibit a clustered, crystalline, faceted, or hedron-like shape rather than a true spherical shape with round and smooth surfaces. They also do not fit the definition of "coral-shaped" nanoparticles, For example, FIG. 1A shows silver nanoparticles formed using a common trisodium citrate method. The nanoparticles are clustered and have a relatively broad size distribution. FIG. 1B shows another set of silver nanoparticles (available from American Biotech Labs, LLC) formed using another chemical synthesis method and showing rough surface morphologies with many edges. FIG. 1C shows a gold nanoparticle having a hedron shape as opposed to a truly "spherical" shape as that term is used and defined herein. FIG. 1D shows a set of silver nanoparticles (sold under the trade name MesoSilver), which have relatively smoother surface morphologies but are understood to be shells of silver formed over a non-metallic seed material.

Figure 2A:
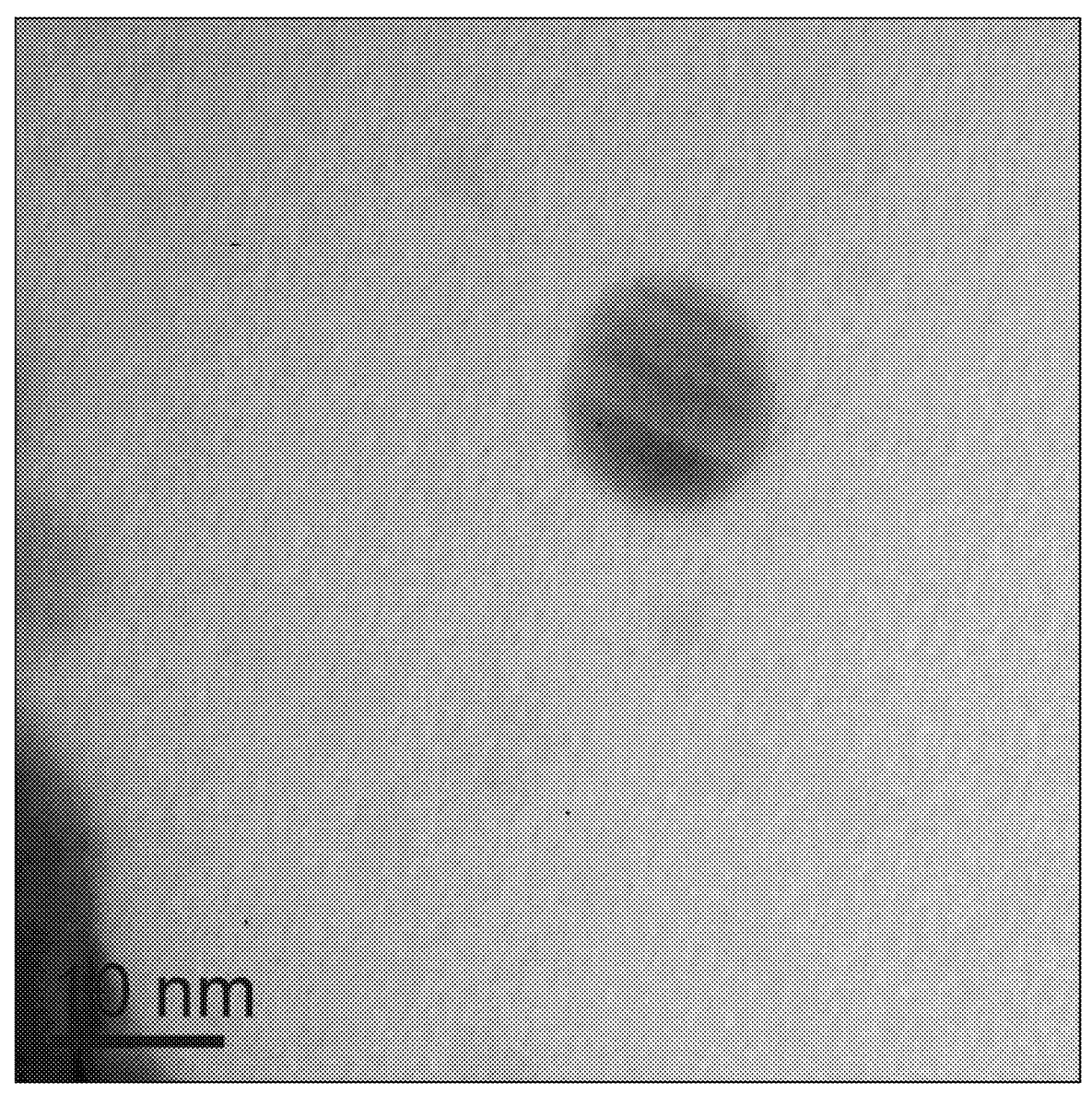
FIGS. 2A-2C show TEM images of exemplary nonionic spherical-shaped metal nanoparticles (i.e., that have no surface edges or external bond angles), the nanoparticles showing substantially uniform size and narrow particle size distribution, smooth surface morphology, and solid metal cores without the use of coating agents or capping agents.
Figure 2B:
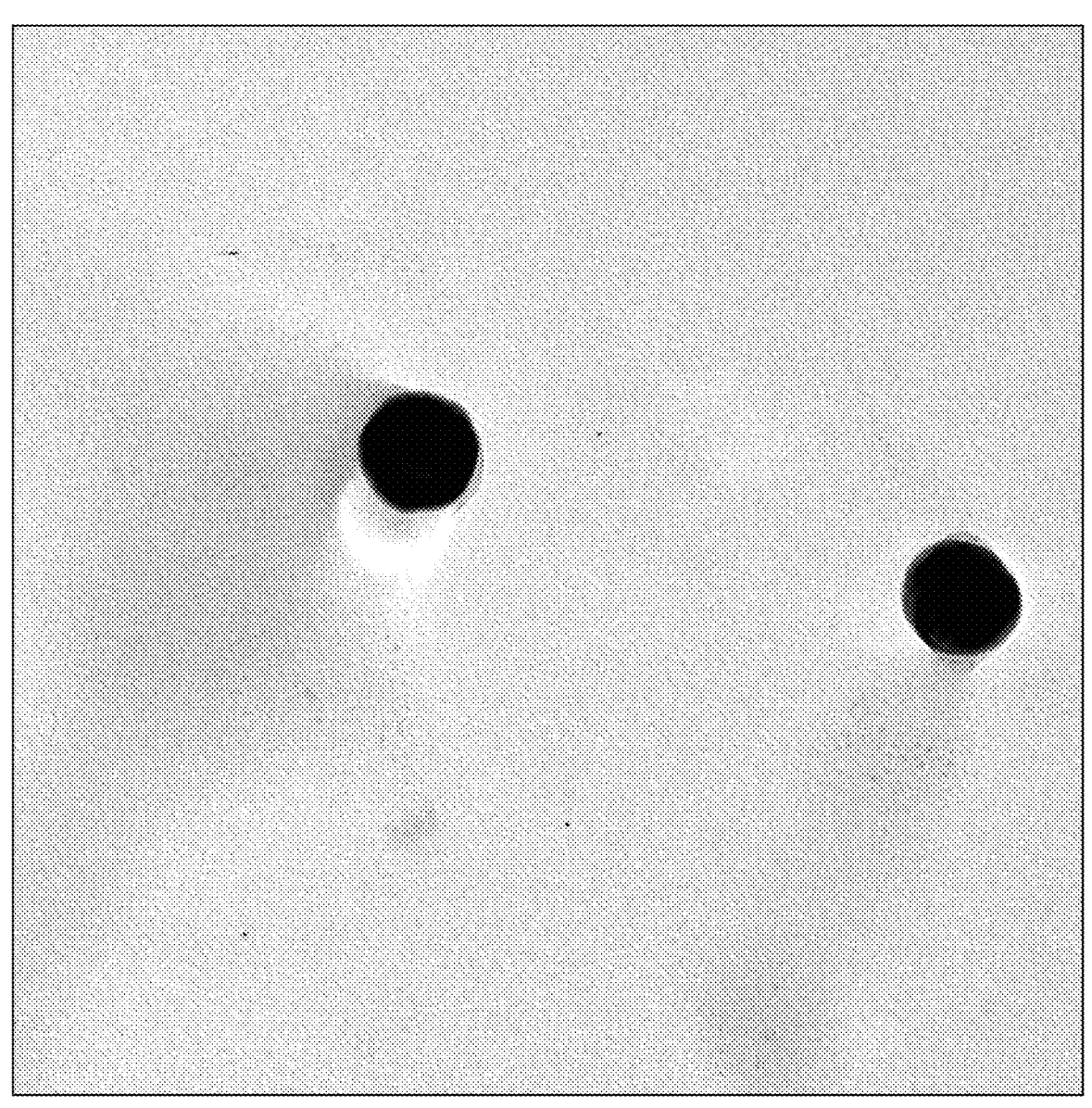
Figure 2C:
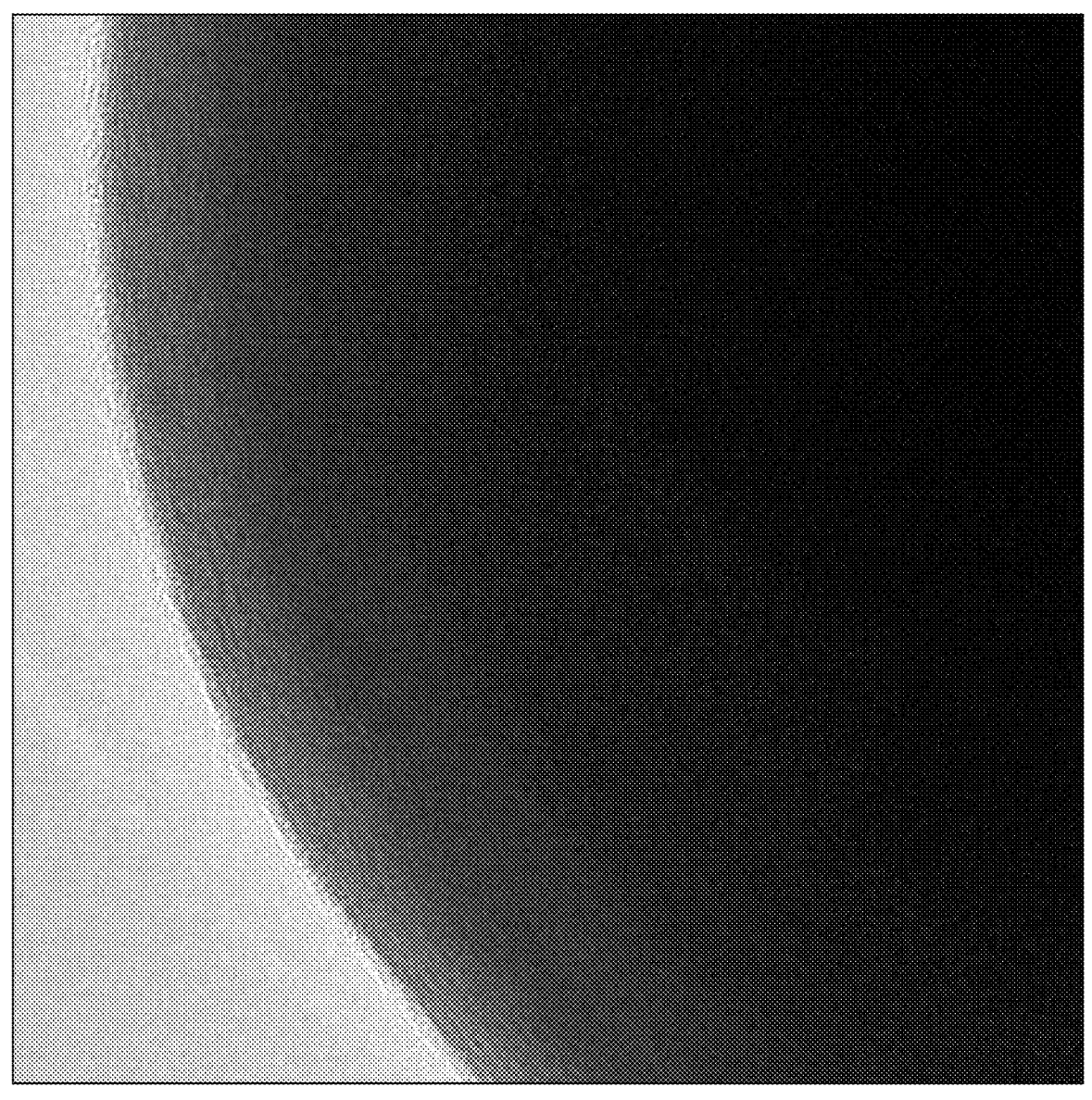

In contrast, the spherical-shaped nanoparticles described herein are solid metal, substantially unclustered, optionally exposed/uncoated, and have a smooth and round surface morphology along with a narrow size distribution. FIGS. 2A-2C show additional TEM images of spherical-shaped nanoparticles used in the present compositions and methods. FIG. 2A shows a gold/silver alloy nanoparticle (90% silver and 10% gold by molarity). FIG. 2B shows two spherical nanoparticles side by side to visually illustrate size similarity. FIG. 2C shows a surface of a metal nanoparticle showing the smooth and edgeless surface morphology.

Figure 3A:
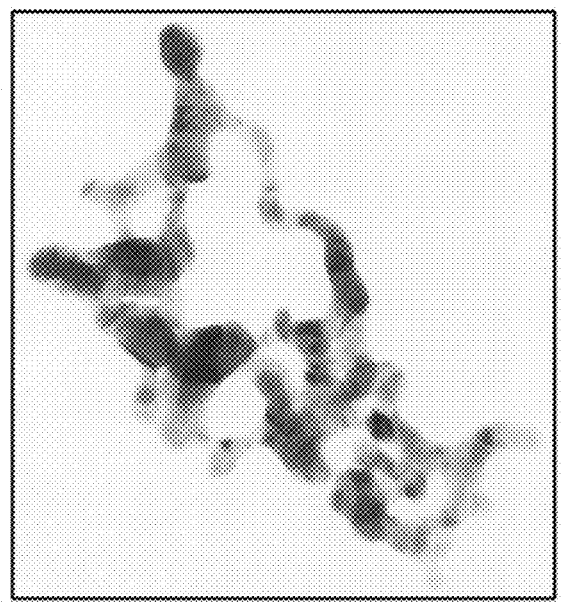
FIGS. 3A-3C show transmission electron microscope (TEM) images of nonionic "coral-shaped" nanoparticles.
Figure 3B:
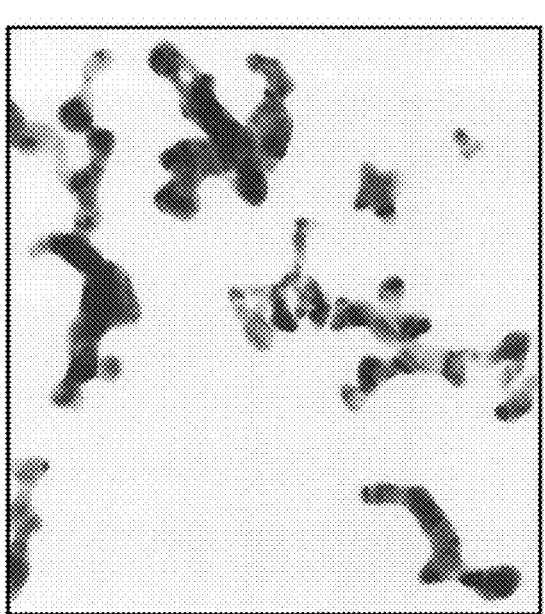
Figure 3C:
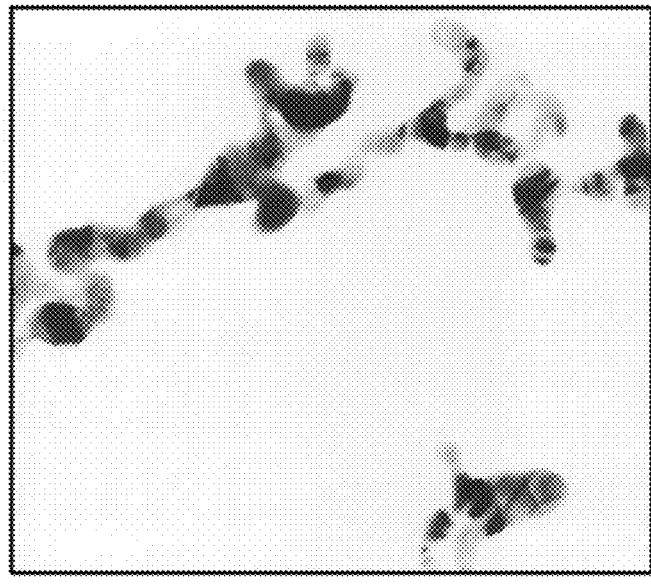

In some embodiments, nonionic metal nanoparticles useful for making nanoparticle compositions may also comprise coral-shaped nanoparticles. The term "coral-shaped metal nanoparticles" refers to nanoparticles that are made from one or more metals, preferably nonionic, ground state metals having a non-uniform cross section and a globular structure formed by multiple, non-linear strands joined together without right angles (see FIGS. 3A-3C). Similar to spherical-shaped nanoparticles, coral-shaped nanoparticles may have only internal bond angles and no external edges or bond angles. Stated differently, such coral-shaped nanoparticles do not have lattice planes or crystalline faces, nor do they depend on crystalline growth based on such structures. This is in contrast to other nanoparticle morphologies such as "nanoflowers" (see, e.g., Sahu et al., "Flower Shaped Nanostructures: An Efficient Bacteria Exterminator" A Search for Antibacterial Agents, Chapter 2, 2007; 73(6): 1712-1720), which include a face centered cubic structure with specified lattice planes. Thus, the term "coral-shaped nanoparticles" excludes the "nanoflowers" disclosed in Sahu et al.

In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising and unexpected result.

In some embodiments, coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV.

Examples of methods and systems for manufacturing coral-shaped nanoparticles are disclosed in U.S. Pat. No. 9,919,363 to William Niedermeyer, which is incorporated by reference.

The metal nanoparticles, including spherical-shaped and coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof.

According to some embodiments, the antimicrobial metal nanoparticles will comprise at least one of silver or gold. In the case of larger metal nanoparticles for use in killing bacteria and fungi, metal nanoparticles may primarily or exclusively comprise silver. However, in the case of smaller metal nanoparticles for use in killing viruses, including Ebola viruses, metal nanoparticles may primarily or exclusively comprise gold. Due to the nature silver and gold atoms making up the nanoparticles, it has been found that gold nanoparticles are better able to hold together at very small sizes (e.g., smaller than about 5-7 nm) compared to silver nanoparticles. On the other hand, in some embodiments, a gold-silver alloy provides the particle stabilizing activity of gold and potentially higher anti-viral activity of silver.

Antimicrobial Activity

Figure 4A:
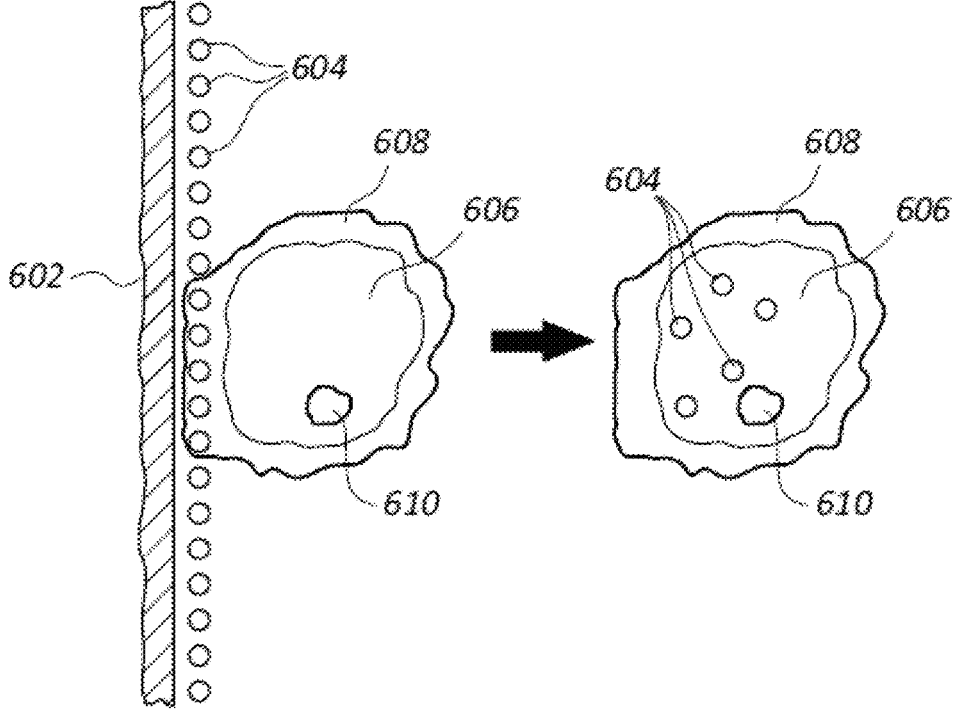
FIGS. 4A-4C schematically illustrated a proposed mechanism of action by which the nanoparticles can kill or deactivate bacteria.

FIG. 4A schematically illustrates a bacterium 608 having absorbed spherical-shaped nanoparticles 604 from a substrate 602 (e.g., from a mucus layer), such as by active absorption or other transport mechanism. The nanoparticles 604 can freely move throughout the interior 606 of bacterium 608 and come into contact with one or more vital proteins or enzymes 610 that, if denatured, will kill or disable the bacterium. A similar mechanism may function where viral or fungal pathogens are involved. Unlike most conventional antibiotics, the nanoparticles effectively kill or deactivate the bacterium without significantly disrupting the cell wall and therefore without significant lysing of the bacteria coming into contact with the nanoparticles.

Figure 4B:
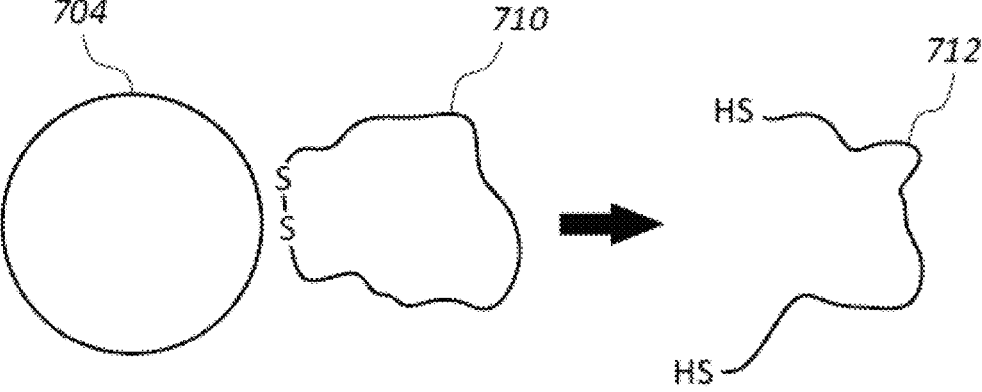

For example, one way that nanoparticles may kill or denature a microbe is by catalyzing the cleavage of disulfide (S—S) bonds within a vital protein or enzyme. FIG. 4B schematically illustrates a microbe protein or enzyme 710 with disulfide bonds being catalytically denatured by an adjacent spherical-shaped nanoparticle 704 to yield denatured protein or enzyme 712. In the case of bacteria or fungi, the cleavage of disulfide bonds and/or cleavage of other chemical bonds of vital proteins or enzymes may occur within the cell interior and thereby function to kill the microbe in this manner without causing significant lysis. Such catalytic cleavage of disulfide (S—S) bonds is facilitated by the generally simple protein structures of microbes, in which many vital disulfide bonds are on exposed and readily cleaved by catalysis.

Another potential mechanism by which metal (e.g., silver) nanoparticles can kill microbes is through the production of active oxygen species, such as peroxides, which can oxidatively cleave protein bonds, including but not limited to amide bonds.

In the case of viruses, spherical-shaped and coral-shaped metal nanoparticles can alternatively deactivate viruses by attaching to glycoproteins and/or catalyzing protein denaturing reactions in the protein coat so that the virus is no longer able to attach to a host cell and/or inject genetic material into the host cell. Because very small nanoparticles can pass through a virus, denaturing of the protein coat may occur within the interior of the virus. A virus that is rendered unable to attach to a host cell and/or inject genetic material into the host cell is essentially inactive and no longer pathogenic.

Figure 4C:
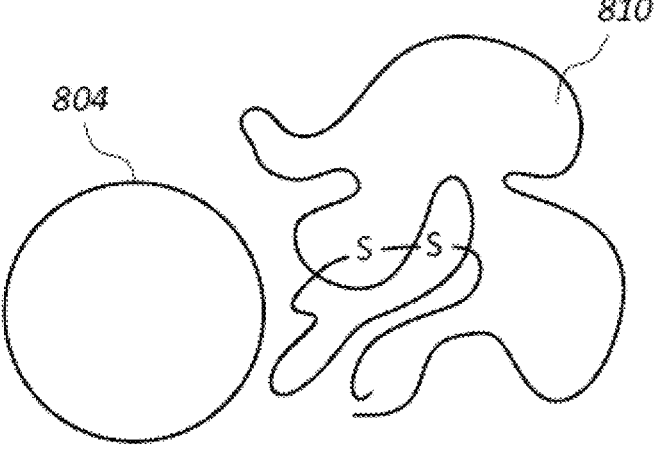

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. FIG. 4C schematically illustrates a mammalian protein 810 with disulfide (S—S) bonds that are shielded so as to resist being catalytically denatured by an adjacent spherical-shaped nanoparticle 804. In many cases the nonionic nanoparticles do not interact with or attach to human or mammalian cells and can be quickly and safely expelled through the urine without damaging kidneys or other cells, tissues, or organs.

The metal nanoparticles kill bacteria without significant release of silver (Ag+) or other metal ions. Because the metal nanoparticles do not release significant quantities of silver or other metal ions, they are essentially non-toxic to humans and other animals (i.e., whatever amount or concentration of ions, if any, that are released from the metal nanoparticles is/are below a threshold toxicity level at which they become toxic to humans, other mammals, birds, reptiles, fish, and amphibians).

In the particular case of silver (Ag) nanoparticles, the interaction of the silver (Ag) nanoparticle(s) within a microbe has been demonstrated to be particularly lethal without the need to rely on the production of silver ions (Ag⁺) to provide the desired antimicrobial effects, as is typically the case with conventional colloidal silver compositions and typical silver nanoparticle compositions. The ability of silver (Ag) nanoparticles to provide effective microbial control without any significant or actual release of toxic silver ions (Ag⁺) into the patient or the surrounding environment is a substantial advancement in the art. Whatever amount or concentration of silver ions released by silver nanoparticles, if any, is well below known or inherent toxicity levels for animals, such as mammals, birds, reptiles, fish, and amphibians.

As used with respect to ion release, the modifying term "significant" means that the effect the term is modifying is clinically noticeable and relevant. Thus, the phrase "without significant release of silver ions" means that though there may technically be some small amount of detectable ion release, the amount is so small as to be clinically and functionally negligible. Similarly, the phrase "without significant cell lysis" means that although there may be some observable cell lysis, the amount is negligible and only tangentially related to the actual primary mechanism of cell death/deactivation.

In contrast, other nanoparticle systems primarily rely on the release of ions for antimicrobial effects. Even though other mechanisms of action are proposed, antimicrobial action via ion release is "one of the most widely accepted"

mechanisms of action. (See Rhim et al. "Preparation and characterization of bio-nanocomposite films of agar and silver nanoparticles: laser ablation method," Carbohydrate Polymers 103 (2014) 456-465). Thus, even if other mechanisms of action may be involved in the antimicrobial activity of silver nanoparticles used in prior methods, the skilled person would not expect particles that do not release silver ions to provide antimicrobial activity to the same degree (or greater degree) than nanoparticles that presumably provide such other mechanisms of action in addition to ion release. In other words, if multiple mechanisms of action are assumed, removing "one of the most widely accepted" mechanisms of action would be expected to lower overall efficacy, even if the other mechanisms remained. One of skill in the art would therefore expect silver nanoparticles that release silver ions to have greater antimicrobial efficacy than silver nanoparticles that are nonionic and do not release any significant amount of silver ions. Surprisingly, however, as shown in the examples herein, nonionic silver nanoparticles made via laser ablation were shown to provide greater antimicrobial efficacy as compared to a standard silver nanoparticle formulation, and even to show antimicrobial efficacy on par with silver nitrate (which is fully ionic).

As discussed herein, the size of the nanoparticles can be selected to target and selectively kill specific types of microbes, including Ebola viruses. By way of further example, sub-micron sized metal nanoparticles (e.g., gold or gold-silver alloy nanoparticles having a diameter of about 0.4 nm) may be most effective in killing Ebola viruses, which have an oddly elongated and looped configuration that can potential shield vital proteins from larger nanoparticles. Using very small nanoparticles as described herein, particularly nonionic metal nanoparticles, permits the nanoparticles to more easily penetrate into and promote denaturing reactions within the protein coat, such as cleavage of disulfide (S—S) bonds in capsid proteins of the virus. Additionally, or alternatively, such nanoparticles can also bind to glycoproteins of the protein coat. For example, nanoparticles having a size of about 2 nm to about 10 nm, or about 4 nm to about 10 nm, or about 6 nm to about 10 nm can bind and/or cleave the 3CSY glycoprotein located on the surface of the Ebola virus. Either or both mechanisms can prevent a virus from attaching to a host cell and introducing its genetic material therein. An Ebola virus that is rendered unable to attach to a host cell and/or inject genetic material into the host cell is essentially inactive and no longer pathogenic.

Microbe-Specific Nanoparticles

Anti-Viral Nanoparticles

In some embodiments, spherical-shaped nanoparticles designed to selectively and preferentially deactivate viruses can have a diameter of about 8 nm or less, such as about 1 nm to about 7 nm, or about 2 nm to about 6.5 nm, or about 3 nm to about 6 nm, or a mean diameter within a range defined using any two of the foregoing values as endpoints. Within these size ranges it is possible to select "designer anti-viral particles" of specific size that are particularly effective in targeting a specific virus. Spherical-shaped nanoparticles within the foregoing ranges, particularly which are smaller than about 6 nm, are significantly less effective in killing fungi and bacteria than the differently sized particles discussed herein that target such other microbes.

Anti-Bacterial Nanoparticles

In some embodiments, spherical-shaped nanoparticles designed to selectively and preferentially deactivate bacteria can have a mean diameter of about 3 nm to about 14 nm, or about 5 nm to about 13 nm, or about 7 nm to about 12 nm, or about 8 nm to about 10 nm, or a mean diameter within a range defined using any two of the foregoing values as endpoints. Within these size ranges it is possible to select "designer anti-bacterial particles" of specific size that are particularly effective in targeting a specific bacterium. Spherical-shaped nanoparticles within the foregoing ranges, particularly which are in a range of about 8 nm to about 10 nm, are significantly less effective in killing viruses and fungi than the differently sized particles discussed herein that target such other microbes.

Anti-Fungal Nanoparticles

In some embodiments, spherical-shaped nanoparticles designed to selectively and preferentially deactivate fungi can have a mean diameter of about 9 nm to about 20 nm, or about 10 nm to about 18 nm, or about 11 nm to about 16 nm, or about 12 nm to about 15 nm, or about 13 nm to about 14 nm, or a mean diameter within a range defined using any two of the foregoing values as endpoints (e.g., 13 nm to 20 nm). Within these size ranges it is possible to select "designer anti-fungal particles" of specific size that are particularly effective in targeting a specific fungus. Spherical-shaped nanoparticles within the foregoing ranges, particularly which are larger than about 12 nm, are significantly less effective in killing viruses and bacteria than the differently sized particles discussed herein that target such other microbes.

According to some embodiments, the antimicrobial metal nanoparticles will comprise at least one of silver or gold. In the case of larger metal nanoparticles for use in killing bacteria and fungi, the metal nanoparticles may primarily or exclusively comprise silver. However, in the case of smaller metal nanoparticles for use in killing viruses, the metal nanoparticles may primarily or exclusively comprise gold. Due to the nature of silver and gold atoms making up the nanoparticles, it has been found that gold nanoparticles are better able to hold together at very small sizes (e.g., smaller than about 5-7 nm) compared to silver nanoparticles. On the other hand, a gold-silver alloy provides the particle stabilizing activity of gold and the higher microbe killing activity of silver.

Multi-Component Nanoparticle Compositions

In some embodiments, coral-shaped metal nanoparticles can be used in conjunction with spherical-shaped metal nanoparticles. In general, spherical-shaped metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical-shaped nanoparticles because coral-shaped nanoparticles have internal spaces and surfaces rather than a solid core and only an external surface. In some cases, providing antimicrobial compositions containing both spherical-shaped and coral-shaped nanoparticles can provide synergistic results. For example, coral-shaped nanoparticles can help carry and/or potentiate the activity of spherical-shaped nanoparticles in addition to providing their own unique benefits.

In some embodiments, the antimicrobial compositions may include both spherical-shaped and coral-shaped nanoparticles. In some embodiments, the mass ratio of spherical-shaped nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1.

Carriers

In some embodiments, a nanoparticle composition includes a carrier for delivering the metal nanoparticles onto or into a living or non-living substrate. The carrier can be a liquid, gel, or solid. Some carriers may be more suitable than others depending on the living or non-living substrate being treated. For example, the solubility characteristics of the carrier can be selected to maximize or otherwise provide a desired diffusion throughout a treated organism part and/or another portion of the organism in contact with the treated organism part.

Examples of compounds that can be utilized for topical applications and can be used as carriers include, but are not limited to, water, alcohols, ketones, esters, citrus oils, essential oils, vegetable and other plant and natural oils, triglycerides, ethers, organic solvents, methanol, ethanol, isopropyl alcohol, other alcohols, glycols, glycerin, polyols, 1,3-propandiol, petroleum jelly, waxes, polymers, polymerizable materials, and surfactants.

In one embodiment, the carrier is a cream or lotion including a glycerin and/or stearic acid cream base optionally containing oils such as coconut oil, olive oil, grape seed oil, shea butter, mango butter, and/or vitamin E oil along with an emulsifying wax.

In other embodiments the carrier is a water or combined water and alcohol solution which itself contains a micro to millimolar concentration of a separate stabilizing agent dissolved into the carrier so as to maintain the nanoparticles within the overall composition.

Exemplary carriers for nasal or pulmonary aerosol or inhalation administration include solutions in saline which can contain, for example, benzyl alcohol or other suitable preservatives, absorption promoters to enhance bioavailability, and/or other solubilizing or wetting or dispersing agents, such as glycerin, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); and glycoaminoglycans and glycosaminoglycan-like compounds (e.g., hyaluronic acid), for example. In some embodiments, the nanoparticles and additional stabilizing agents and/or carriers are formulated as dry powders (e.g., powders useful for administering with dry powder inhalers).

Exemplary aerosols useful for nasal and/or inhalation administration include a vaporizable propellant, such as low molecular weight hydrofluorocarbons or hydrocarbons that are liquid when constrained in a suitable container and are biocompatible and non-irritating. Ingredients such as water, alcohol, propylene glycol, and polyethylene glycols can be additionally included. Other embodiments, also useful for nasal and/or inhalation administration, are provided as sprays (e.g., omitting an aerosol propellant). Such spray formulation may be provided as a solution, suspension, or emulsion capable of forming a fine mist for administration, and in some embodiments, may include saline and/or be isotonic.

Exemplary injectable solutions include an aqueous emulsion or oleaginous suspension or saline solution (e.g., isotonic, hypotonic, or hypertonic, optionally including dextrose and/or other electrolytes or additives). Such compositions can also include suitable dispersing or wetting agents. The sterile injectable preparation may also be formed in a non-toxic parenterally acceptable diluent or solvent, such as a solution in 1,2-propanediol (propylene glycol). Additional examples include solutions or suspensions which can contain, for example, suitable non-toxic diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Gels known in the art can be used as carriers, such as gels containing one or more of the foregoing liquid components together with known gelling agents. Gel compositions can more easily adhere to a living or non-living substrate being treated. An exemplary gel carrier can include mineral oil gelled with polyethylene.

Solid carriers can be used for different reasons, such as to elute nanoparticles into an organism over time. Examples of solid carriers include, but are not limited to, polymers, rubbers, elastomers, foams, and gums. Depending on the characteristics of the organism to be treated and the desired rate of elution, one of skill in the art can select an appropriate solid carrier material.

In some embodiment, an antimicrobial composition can be formulated so that the metal nanoparticles are included in a concentration so that a measured quantity of the nanoparticle composition, when applied onto or into an organism or organism part, will provide a predetermined concentration or quantity of metal nanoparticles. The nanoparticle composition can have a higher concentration of nanoparticles that become diluted when mixed with other liquids applied to or naturally contained within the organism or organism part. Depending on the organism or organism part being treated, the nature of the nanoparticles being added, and the type of carrier being used, the antimicrobial composition may contain about 10 ppb (parts per billion) to about 100 ppm (parts per million) by weight of the antimicrobial composition, or about 15 ppb to about 90 ppm, or about 100 ppb to about 75 ppm, or about 500 ppb to about 60 ppm of metal nanoparticles by weight, or about 1 ppm to about 50 ppm, or about 2 ppm to about 25 ppm, or about 3 ppm to about 20 ppm metal nanoparticles by weight of the antimicrobial composition.

In some embodiments, the antimicrobial composition can also include one or more optional components or adjuvants to provide desired properties, including, but not limited to food, vitamins, minerals, antimicrobial agents, electrolytes, moisturizers, emollients, antiseptics, and/or plant extracts.

In some embodiments, the carrier may also function as, or may include, a stabilizing agent. For example, in some embodiments it may be desirable to have different specifically sized nanoparticles within the same solution to take advantage of each of the different properties and effects of the different particles. However, when differently sized particles are mixed into a single solution, the overall long-term stability of these particles within that single solution may be substantially diminished as a result of unequal forces exerted on the various particles causing eventual agglomeration of the particles. This phenomenon may become even more pronounced when that solution is either heated or cooled significantly above or below standard room temperature conditions.

Examples of stabilizing agents include alcohols (e.g., ethanol, propanol, butanol, etc.), polyphenols (e.g., arjuna bark extract, grape seed extract, etc.), mono-glycerides, di-glycerides, or triglycerides (e.g., grape seed oil, coconut oil, and the like), oils (e.g., lavender), other terpenes, amine compounds (e.g., mono-, di-, or tri-ethanol amine), carbohydrates (e.g., sucrose, fructose), liposomes, creams, other emulsions, and other polymers.

In some embodiments, stabilizing agents are dissolved within a separate carrier in the micro- to milli-molar concentration range with the upper range limitation typically being constrained not by efficacy but by product cost.

These various stabilizing agents have the capacity to hold the at least two differently sized and/or shaped nanoparticles in suspension and deliver these nanoparticles into the treatment area of a person or animal without so powerfully retaining the nanoparticles so as to diminish the antimicrobial properties of the nanoparticles.

Treatment Methods

In some embodiments, a method of method of killing or deactivating a microbe comprises: (1) applying an antimicrobial composition comprising a carrier and metal nanoparticles onto or into a substrate containing microbes; and (2) the antimicrobial composition killing or denaturing the microbes. The substrate can be a living organism, such as an organism that is infected with, or may become infected with, a disease caused by a microbe. Alternatively, the substrate can be a non-living object that has come into contact, or is at risk of coming into contact, with a disease causing or otherwise unwanted microbe, such as clothing, bedding, wound dressings, medical devices or implants, food, intravenously injectable liquids, farm equipment, animal feeding devices, watering troughs, and the like.

In some embodiments, metal nanoparticles kill bacteria or fungi by entering the cell and catalyzing protein denaturing reactions. In some embodiments, metal nanoparticles "deactivate" viruses by attaching to glycoproteins and/or catalyzing protein denaturing reactions in the protein coat. Examples of protein denaturing reactions include reactions involving one or more of disulfide (S—S) bond cleavage and formation of active oxygen species that attack amide or other bonds.

In some embodiments, a method of deactivating a virus comprises: (1) applying an anti-viral composition comprising metal nanoparticles having a selected particle size onto or into a substrate containing a virus, and (2) the anti-viral composition deactivating the virus.

In some embodiments, a method of deactivating Ebola viruses comprises: (1) applying an anti-viral composition comprising a carrier and metal nanoparticles onto or into an animal or non-living substrate contaminated with Ebola viruses; and (2) the metal nanoparticles deactivating Ebola viruses by attaching to glycoproteins and/or denaturing one or more proteins in the Ebola viruses. The substrate can be a living organism, such as an organism that is infected with, or may become infected with, Ebola viruses. Alternatively, the substrate can be a non-living object that can come into contact with an organism and potentially cause or spread disease, such as clothing, beading, wound dressing, medical device or implant, food, IV liquid, farm equipment, animal feeding devices, watering troughs, and the like.

In some embodiments, metal nanoparticles deactivate viruses by attaching to glycoproteins and/or catalyzing protein denaturing reactions in the protein coat. Examples of protein denaturing reactions include reactions involving one or more of disulfide (S—S) bond cleavage and formation of active oxygen species that attack amide or other bonds.

In some embodiments, the method may comprise administering a pharmaceutically acceptable quantity of the antiviral composition to a mammal in order to treat or prevent Ebola virus disease. The anti-viral composition can be administered in any appropriate fashion, including but not limited to, intravenously, via inhalation, orally, and/or topically. Advantageously, the metal nanoparticles selectively deactivate Ebola viruses without harming humans or animals contacting the metal nanoparticles.

In some embodiments, the method may comprise applying the anti-viral composition to one or more of medical equipment, clothing, bandages, waste receptacles, syringes, syringe needles, inhalation equipment, or implants.

In some embodiments, a method of treating or preventing Ebola virus disease comprises: (1) administering a pharmaceutically acceptable quantity of spherical-shaped nonionic metal nanoparticles having a particle size in a range of about 0.22 nm to about 2 nm to a living organism, and (2) the anti-viral composition deactivating the virus.

In some embodiments, a method of killing a bacterium comprises: (1) applying an anti-bacterial composition comprising metal nanoparticles having a selected particle size onto or into a substrate containing a bacterium, and (2) the anti-bacterial composition killing the bacterium.

In some embodiments, a method of killing a fungus comprises: (1) applying an anti-fungal composition comprising metal nanoparticles having a selected particle size onto or into a substrate containing a fungus, and (2) the anti-bacterial composition killing the fungus.

EXAMPLES

In the following examples, the nonionic, ground state, uncoated metal nanoparticles described above may be referred to as "Attostat" nanoparticles, "Niedermeyer" nanoparticles, "Attostat Ag," or the like. Except where noted otherwise, the Attostat nanoparticles utilized were spherical, silver nanoparticles having a mean diameter ranging from 6 nm to 10 nm.

Example 1

Testing measured the transepithelial electrical resistance (TER) of a nanoparticle composition applied to the apical surface of cystic fibrosis patient derived primary cultures of bronchial epithelia (maintained in ALI cultures). TER is a measure of epithelial tight junction integrity which underlies the physical barrier function of airway epithelia. Changes in TER of 12 epithelia were observed over 24 hours.

Changes in measured TER of epithelia treated with spherical, nonionic, ground state silver nanoparticle formulations at 3 ppm were not significantly different from the responses to vehicle treatment at the sampled time points, as determined with ANOVA and Turkey-Kramer HSD post-test analysis with $P<0.05$. The impact of the silver nanoparticle formulations on the barrier function of well differentiated primary CF bronchial epithelia was therefore not distinct from the impact of vehicle treatment.

Further, there were no visually distinct differences in microscopic appearance of the epithelia at about 100× magnification in a phase contrast microscope. Ciliary activity was also similar across treatment groups. These results were surprising given the general belief that silver nanoparticles of such size would release silver ions and be toxic to such cells.

Example 2

This test compared the effect on zebra fish of nonionic, ground state silver nanoparticles formed via laser ablation compared to other silver nanoparticles formed through conventional chemical synthesis or electrolysis methods, silver nitrate, and a control tank with plain water. The nanoparticles formed through a chemical synthesis process and the nanoparticles formed through an electrolysis process both caused the fish to exhibit signs of toxicity, including death, slowed movement and settling near the bottom of the tank. The nanoparticles formed through an electrolysis process and the silver nitrate both killed the fish within 2 hours of exposure.

In contrast, the fish in the tank treated with the nonionic, ground state silver nanoparticles of the present application and the fish in the control tank were equally healthy and active. None of the zebrafish exposed to the nonionic, ground state silver nanoparticles of the present application died during the course of the study, whereas all other treatments were associated with at least some zebrafish death.

The results of the zebrafish study were surprising in light of the general knowledge that silver nanoparticles show toxicity in such studies. For example, the authors of Mansouri et al., "Effects of Short-Term Exposure to Sublethal Concentrations of Silver Nanoparticles on Histopathology and Electron Microscope Ultrastructure of Zebrafish (Danio Rerio) Gills," *Iranian J. Toxicity*, Vol. 10, No 1, January-February 2016, state the concern that "[t]he increasing use of nanomaterials and nanoproducts has increased the possibility of contamination of the environment, which may have adverse effects on different organisms" (Abstract). The authors concluded, following the study, that "[b]ased on the adverse effects of AgNPs [silver nanoparticles] on zebrafish gills, silver nanoparticle solutions can be hazardous pollutants for the environment" (page 15).

Example 3

Neutrophil testing was done using complete blood count (CBC) analysis. Testing 0.2 and 1.0 μg/mL (i.e., ppm) of Attostat Ag showed that after up to 6 hours exposure time, no blood panel values deviated from normal ranges. At 24 hours exposure time, both control and test samples showed borderline values for MCHC (Mean Corpuscular Hemoglobin Concentration, just below minimum normal range) and MPV (Mean Platelet Volume, just above the maximum normal range).

The only deviation from normal values occurred in the 0.2 μg/mL Attostat Ag sample, which exhibited very slight elevation in EOS % (Eosinophil Percentage, just above maximum normal range). Overall, these results show no significant toxicological effects on the full spectrum of blood cells and components. This is particularly encouraging as forecasted therapeutics typically would not exceed 8-10 μg/mL, resulting in much lower local concentrations throughout the bloodstream and other portions of the body.

Example 4

Figure 5:
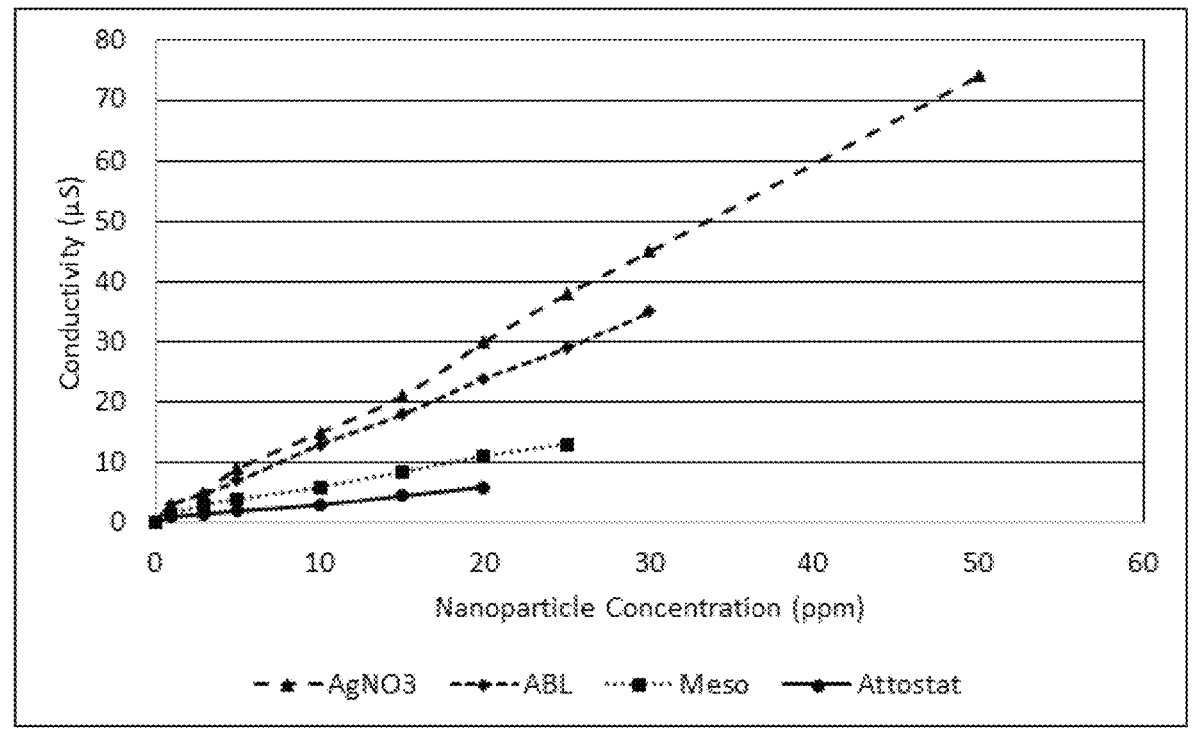
FIG. 5 illustrates the results of conductivity testing comparing various nanoparticle solutions and showing that spherical, metal nanoparticles according to the disclosed embodiments are nonionic.

FIG. 5 illustrates the results of conductivity testing comparing various nanoparticle solutions. In the Figure, "Attostat" corresponds to spherical-shaped, nonionic silver nanoparticles formed by laser ablation such as described herein, "AgNO$_3$" is silver nitrate, "Meso" represents a commercially available silver nanoparticle formulation with nanoparticles formed through a chemical reduction process, and "ABL" represents a commercially available silver nanoparticle formulation understood to be formed through an electrolysis process.

The results illustrate that the Attostat nanoparticle formulation had significantly less ion release than any of the other tested nanoparticle formulations. It should be noted that the measured conductivity for Attostat nanoparticle formulations, even at the highest measured concentration of 16 ppm, remained low enough to be on par with typical conductivity measurements for high quality deionized water.

Example 5

An antibacterial efficacy test was carried out comparing a "Niedermeyer" nanoparticle formulation (8 nm size) against silver nitrate and against the National Institute of Standards and Technology (NIST) Standard Nanocomposix 10 nm silver nanoparticles. The NIST nanoparticles are formed by a chemical reduction process that utilizes citrate as reducing and capping agent. The NIST nanoparticles have a conductivity similar to the "Meso" nanoparticles of Example 4, with detectable but low levels of silver ions.

Relative Light Unit (RLU) counts were recorded at 12 hours and 24 hours post treatment. RLU measurements were carried out using a Hygiena SystemSURE Plus V.2 SN067503 RLU meter with Hygenia AquaSnap TOTAL ATP Water Test Cat #U143 Lot #153019. Culturing media was Hardy Diagnostics Buffered Peptone Water Lot #118272. Samples were prepared with the nanoparticle treatments and then diluted with the media to provide the tested concentrations. The test organism (Microbiologics, *E. coli*, KwikStik, ATCC #51813, Ref #0791 K, Lot #791-1-6) was incubated in fresh Buffered Peptone Water growth media for 24 hours prior to exposure to the nanoparticle treatments. Tables 1 and 2 illustrate results of RLU counts 12 and 24 hours post nanoparticle treatment, respectively.

TABLE 1

RLU Counts at 12 Hours Post Exposure to Nanoparticle Treatment

| Concentration | Attostat 8 nm Particles | NIST Standard Particles 10 nm | AgNO3 Silver Nitrate |
|---|---|---|---|
| Control 0 ppm (mg/L) | 6256 | 7037 | 6731 |
| 0.25 ppm (mg/L) | 65 | 6908 | 80 |
| 0.5 ppm (mg/L) | 72 | 5416 | 75 |
| 1.0 ppm (mg/L) | 30 | 7189 | 84 |

TABLE 2

RLU Counts at 24 Hours Post Exposure to Nanoparticle Treatment

| Concentration | Attostat 8 nm Particles | NIST Standard Particles 10 nm | AgNO3 Silver Nitrate |
|---|---|---|---|
| Control 0 ppm (mg/L) | 7595 | 5421 | 7342 |
| 0.25 ppm (mg/L) | 25 | 5691 | 25 |
| 0.5 ppm (mg/L) | 8 | 3950 | 46 |
| 1.0 ppm (mg/L) | 30 | 3834 | 30 |

Tables 3 and 4 represent the data in terms of comparing each treatment to its respective control at 12 and 24 hours post treatment, respectively.

TABLE 3

RLU as percentage of control at 12 Hours Post Treatment

| Concentration | Attostat 8 nm Particles | NIST Standard Particles 10 nm | AgNO3 Silver Nitrate |
|---|---|---|---|
| Control 0 ppm (mg/L) | 100% | 100% | 100% |
| 0.25 ppm (mg/L) | 1.0% | 98.2% | 1.2% |
| 0.5 ppm (mg/L) | 1.1% | 77.0% | 1.1% |
| 1.0 ppm (mg/L) | 0.6% | 102.2% | 1.3% |

TABLE 4

RLU as percentage of control at 24 Hours Post Treatment

| Concentration | Attostat 8 nm Particles | NIST Standard Particles 10 nm | AgNO3 Silver Nitrate |
|---|---|---|---|
| Control 0 ppm (mg/L) | 100% | 100% | 100% |
| 0.25 ppm (mg/L) | 0.33% | 105% | 0.34% |
| 0.5 ppm (mg/L) | 0.11% | 72.9% | 0.62% |
| 1.0 ppm (mg/L) | 0.39% | 70.7% | 0.41% |

As shown, at all concentrations tested, the Attostat nanoparticles reduced the number of RLU counts to less than 1.5% from the control baseline at both the 12 hour and 24 hour measurement periods. Anything below 1.5% is below level of accurate detection and is considered a complete kill.

The Attostat nanoparticles effectively reduced RLU counts to below the 1.5% threshold at all tested concentrations. The NIST nanoparticles appeared to show a trend toward greater efficacy at higher concentrations, which would correspond to a normal diffusion model, but even at the highest tested concentration still only reached an RLU count of 70.7% of the initial control baseline at the 24 hour measurement.

The low antimicrobial efficacy of the NIST nanoparticles at the concentrations tested as compared to the silver nitrate could potentially be explained by the lower conductivity, and thus lower ion concentration, of the NIST nanoparticles as compared to the silver nitrate. However, the significant efficacy of the Attostat nanoparticles was surprising given the fact that the Attostat nanoparticles have significantly low to non-detectable levels of ions, even lower than the NIST particles. The Attostat nanoparticles continued to provide antimicrobial activity through the 24-hour testing period with no signs of reduced efficacy.

Example 6

An assay for antiviral activity is designed to test and compare the antiviral activity of nanoparticle compositions of different sizes. All tested nanoparticle compositions are spherical, metal nanoparticles formed via laser ablation as described herein. A first test composition includes nanoparticles with a mean diameter of 4 nm. A second test composition includes nanoparticles with a mean diameter of 8 nm. A third test composition includes nanoparticles with a mean diameter of 14 nm. All reagents, test microbes, concentrations, treatment duration, and other test protocols are held the same across tests. The first test composition, with mean particle diameter of 4 nm, has greater antiviral activity than the second test composition (mean particle diameter 8 nm) or the third test composition (mean particle diameter 14 nm).

Example 7

An assay for antibacterial activity is designed to test and compare the antibacterial activity of nanoparticle compositions of different sizes. All tested nanoparticle compositions are spherical, metal nanoparticles formed via laser ablation as described herein. A first test composition includes nanoparticles with a mean diameter of 4 nm. A second test composition includes nanoparticles with a mean diameter of 8 nm. A third test composition includes nanoparticles with a mean diameter of 14 nm. All reagents, test microbes, concentrations, treatment duration, and other test protocols are held the same across tests. The second test composition, with mean particle diameter of 8 nm, has greater antibacterial activity than the first test composition (mean particle diameter 4 nm) or the third test composition (mean particle diameter 14 nm).

Example 8

An assay for antifungal activity is designed to test and compare the antifungal activity of nanoparticle compositions of different sizes. All tested nanoparticle compositions are spherical, metal nanoparticles formed via laser ablation as described herein. A first test composition includes nanoparticles with a mean diameter of 4 nm. A second test composition includes nanoparticles with a mean diameter of 8 nm. A third test composition includes nanoparticles with a mean diameter of 14 nm. All reagents, test microbes, concentrations, treatment duration, and other test protocols are held the same across tests. The third test composition, with mean particle diameter of 14 nm, has greater antifungal activity than the first test composition (mean particle diameter 4 nm) or the second test composition (mean particle diameter 8 nm).

Example 9

Nonionic spherical silver nanoparticles having a mean particle size in a range of about 8 nm to about 10 nm, in which at least 99% of the silver nanoparticles have a particle size that is within ±1 nm of the mean diameter, are highly effective in targeting and killing bacteria. They are significantly more effective at killing bacteria at lower concentrations compared to silver nanoparticles having greater size variability. They are also significantly more effective at killing bacteria than either viruses or fungi.

Example 10

Nonionic spherical silver nanoparticles having a mean particle size in a range of about 3 nm to about 6 nm, in which at least 99% of the silver nanoparticles have a particle size that is within ±1 nm of the mean diameter, are highly effective in targeting and killing viruses. They are significantly more effective at killing viruses at lower concentrations compared to silver nanoparticles having greater size variability. They are also significantly more effective at killing viruses than either bacteria or fungi.

Example 11

Nonionic spherical silver nanoparticles having a mean particle size in a range of about 12 nm to about 15 nm, in which at least 99% of the silver nanoparticles have a particle size that is within ±1 nm of the mean diameter, are highly effective in targeting and killing fungi. They are significantly more effective at killing fungi at lower concentrations compared to silver nanoparticles having greater size variability. They are also significantly more effective at killing fungi than either viruses or bacteria.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of killing or deactivating a target microbe, comprising:
   (i) selecting a bacterium as the target microbe to be killed or deactivated;
   (ii) providing an antimicrobial composition that kills or deactivates the bacterium, the antimicrobial composition comprising:
   a carrier; and
   a plurality of spherical-shaped, nonionic metal nanoparticles formed from silver or a silver alloy, formed by laser ablation, and having a mean diameter in a range of 7 nm to 12 nm to kill or deactivate the selected bacterium, wherein at least 99% of the spherical-shaped, nonionic metal nanoparticles have a diameter within +3 nm of the mean diameter, wherein the spherical-shaped, nonionic metal nanoparticles are present in the antimicrobial composition in a concentration of about 0.25 ppm to about 201 ppm;
   (iii) applying the antimicrobial composition to the bacterium or to a substrate containing the bacterium; and
   (iv) the metal nanoparticles killing or deactivating the bacterium without significant release of silver ions and with greater efficacy than chemically synthesized silver nanoparticles at the same concentration.

2. The method of claim 1, wherein the metal nanoparticles have a mean diameter in a range of 8 nm to 10 nm, and wherein at least 99% of the metal nanoparticles have a particle size within 30% of the mean diameter.

3. The method of claim 1, wherein the antimicrobial composition further comprises coral-shaped metal nanoparticles formed via laser ablation without crystalline growth, the coral-shaped metal nanoparticle having a non-uniform cross section and a globular structure formed by multiple, non-linear strands joined together without right angles.

4. The method of claim 1, wherein the spherical-shaped, nonionic metal nanoparticles comprise silver, gold, or an alloy of silver and gold.

5. The method of claim 1, wherein the carrier is a liquid in which the metal nanoparticles are colloidally dispersed.

6. The method of claim 1, wherein the substrate is a non-living object.

7. The method of claim 1, wherein the substrate is a living organism.

8. A method of killing or deactivating a target microbe, comprising:
   (i) selecting a bacterium as the target microbe to be killed or deactivated;
   (ii) providing an antimicrobial composition that kills or deactivates the bacterium, the antimicrobial composition comprising:
   a carrier; and
   a plurality of spherical-shaped, nonionic metal nanoparticles formed from silver or a silver alloy, formed by laser ablation, and having a mean diameter in a range of 7 nm to 12 nm to kill or deactivate the selected bacterium, wherein at least 99% of the spherical-shaped, nonionic metal nanoparticles have a diameter within 30% of the mean diameter, wherein the plurality of spherical-shaped, nonionic metal nanoparticles are present in the antimicrobial composition in a concentration of about 0.25 ppm to about 1 ppm, wherein the antimicrobial composition is non-toxic to humans and other animals;

(iii) applying the antimicrobial composition to the bacterium or to a substrate containing the bacterium; and (iv) the metal nanoparticles killing or deactivating the bacterium without significant release of silver ions and without toxic effects to humans or other animals, wherein the antimicrobial composition reduces a number of Relative Light Unit counts to less than 1.5% from a control baseline at a 24-hour measurement period, the control baseline containing no spherical-shaped, nonionic metal nanoparticles.

9. The method of claim 8, wherein the antimicrobial composition further comprises coral-shaped metal nanoparticles formed via laser ablation without crystalline growth, the coral-shaped metal nanoparticle having a non-uniform cross section and a globular structure formed by multiple, non-linear strands joined together without right angles.

10. The method of claim 8, wherein the spherical-shaped, nonionic metal nanoparticles comprise silver, gold, or an alloy of silver and gold.

11. The method of claim 8, wherein the carrier is a liquid in which the metal nanoparticles are colloidally dispersed.

12. The method of claim 8, wherein the substrate is a non-living object.

13. The method of claim 8, wherein the substrate is a living organism.

14. The method of claim 8, wherein the antimicrobial composition is formulated to exhibit antibacterial efficacy against *Escherichia coli* at concentrations of 0.25 ppm by reducing a viable bacterial activity to below 1.5% of untreated controls within 24 hours.

15. The method of claim 8, wherein the antimicrobial composition is formulated to exhibit no observable toxicological effects in aquatic organisms after 24 hours of exposure.

16. The method of claim 8, wherein the antimicrobial composition is formulated to exhibit no significant toxicological effects on a full spectrum of blood cells after 24 hours of exposure.

17. A method of killing or deactivating a target microbe, comprising:

(i) selecting a bacterium comprising *Escherichia coli* as the target microbe to be killed or deactivated;

(ii) providing an antimicrobial composition that kills or deactivates the bacterium, the antimicrobial composition comprising:

a carrier; and a plurality of spherical-shaped, nonionic metal nanoparticles formed from silver or a silver alloy, formed by laser ablation, and having a mean diameter in a range of 7 nm to 12 nm to kill or deactivate the selected bacterium, wherein at least 99% of the spherical-shaped, nonionic metal nanoparticles have a diameter within 30% of the mean diameter, wherein the plurality of spherical-shaped, nonionic metal nanoparticles are present in the antimicrobial composition in a concentration of about 0.25 ppm to about 20 ppm, wherein the antimicrobial composition is non-toxic to humans and other animals;

(iii) applying the antimicrobial composition to the bacterium or to a substrate containing the bacterium; and (iv) the metal nanoparticles killing or deactivating the bacterium without significant release of silver ions and without toxic effects to humans or other animals, wherein the antimicrobial composition reduces a number of Relative Light Unit counts to less than 1.5% from a control baseline at both a 24-hour measurement period, the control baseline containing no spherical-shaped, nonionic metal nanoparticles.

* * * * *